(12) United States Patent
Mahaney et al.

(10) Patent No.: US 7,351,709 B2
(45) Date of Patent: Apr. 1, 2008

(54) ESTROGEN RECEPTOR LIGANDS

(75) Inventors: Paige Erin Mahaney, Pottstown, PA (US); Michael Byron Webb, Levittown, PA (US); Fei Ye, Audubon, PA (US); Joseph Peter Sabatucci, Collegeville, PA (US)

(73) Assignee: Wyeth, Madison, NJ (US)

( * ) Notice: Subject to any disclaimer, the term of this patent is extended or adjusted under 35 U.S.C. 154(b) by 251 days.

(21) Appl. No.: 11/147,489

(22) Filed: Jun. 8, 2005

(65) Prior Publication Data
US 2006/0019961 A1 Jan. 26, 2006

Related U.S. Application Data

(60) Provisional application No. 60/578,179, filed on Jun. 9, 2004.

(51) Int. Cl.
*A01N 43/58* (2006.01)
*A01N 43/60* (2006.01)
*A61K 31/50* (2006.01)
*A61K 31/495* (2006.01)
*C07D 241/36* (2006.01)

(52) U.S. Cl. ...................... 514/249; 544/353
(58) Field of Classification Search ...................... None
See application file for complete search history.

(56) References Cited

U.S. PATENT DOCUMENTS

| | | | |
|---|---|---|---|
| 3,479,348 A | 11/1969 | Yamamoto | 544/354 |
| 5,723,461 A | 3/1998 | Rosner | 514/249 |
| 6,369,057 B1 | 4/2002 | Billhardt et al. | 514/234.8 |
| 6,908,921 B2 * | 6/2005 | Su et al. | 514/249 |
| 7,056,937 B2 * | 6/2006 | Grant et al. | 514/353 |
| 7,183,281 B2 * | 2/2007 | Grant et al. | 514/249 |

FOREIGN PATENT DOCUMENTS

| | | |
|---|---|---|
| DE | 197 03 131 A1 | 7/1998 |
| EP | 0 266 102 B1 | 3/1993 |
| EP | 0 728 481 A2 | 8/1996 |
| EP | 0 509 398 B1 | 9/2001 |
| EP | 0 620 216 B1 | 1/2003 |
| EP | 0 657 166 B1 | 4/2003 |
| JP | 4321669 | 11/1992 |
| WO | 91/05549 A1 | 5/1991 |
| WO | 92/16524 A1 | 10/1992 |
| WO | 96/33723 A2 | 10/1996 |

OTHER PUBLICATIONS

Romanenko et al, "Condensed and bound quinoxalines. IV. New pathway to acrylamides of (1,2-dihydro-2-oxo-3-quinoxalinyl) acetic acid" Khimiya Geterotsiklicheskikh Soedinenii, vol. 2, pp. 264-266 (1973). English Translation.*

Tatchum-Talom et al, "Acute vascular effects of the selective estrogen receptor modulator EM-652 (SCH 57068) in the rat mesenteric vascular bed" Cardiovascular Research, vol. 57(2), pp. 535-543 (2003).*

Mahaney et al, "Synthesis and activity of a new class of pathway-selective estrogen receptor ligands: Hydroxybenzoyl-3,4-dihydroquinoxalin-2(1H)-ones" Bioorganic & Medicinal Chemistry, vol. 14, pp 3455-3466 (2006).*

Adams, M. R. et al., "Inhibition of Coronary Artery Atherosclerosis by 17-beta Estradiol in Ovariectomized Monkeys," *Arterio.*, 1990, 10(6), 1051-1057.

Alexander et al., "Initiation of Hormone Replacement Therapy After Acute Myocardial Infarction Is Associated With More Cardiac Events During Follow-Up," *J. Am. Coll. Cardio.*, 2001, 38, 1-7.

Bauer M. A., Herrmann F., "Interleukin-6 in clinical medicine," *Ann. Hematol.*, 1991, 62, 2003-210.

Brooks, P.R. et al., "Boron Trichloride/Tetra-*n*-Butylammonium Iodide: A Mild, Selective Combination Reagent for the Cleavage of Primary Alkyl Aryl Ethers," *J. Org. Chem.* 1999, 64, 9719-9721.

Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).

Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4):285-298.

Bundgaard, H., "Means to enhance penetration; Prodrugs as a means to improve the delivery of peptide drugs," *Advanced Drug Deliver Reviews*, 1992, 8, 1-38.

Cefalu, W., "The Use of Hormone Replacement Therapy in Postmenopausal Women with Type 2 Diabetes," *J Womens Health & Gender-based Med.*, 2001, 10(3), 241-255.

Lin, C. C. et.al., "Pulmonary function changes and increased Th-2 cytokine expression and nuclear factor kB activation in the lung after sensitization and allergen challenge in brown Norway rats," *Immunol. Lett.*, 2000, 73, 57-64.

(Continued)

*Primary Examiner*—Zachary C Tucker
(74) *Attorney, Agent, or Firm*—Pepper Hamilton LLP

(57) ABSTRACT

The present invention relates to estrogen receptor ligands, and compounds and methods for treating diseases associated with excessive estrogen receptor activity. Compound of the formula I are disclosed:

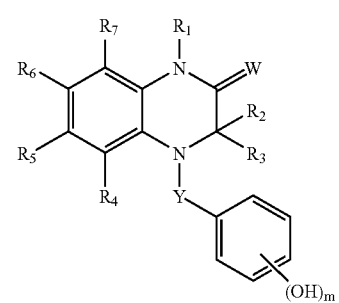

wherein W is O or $(CR_8)_2$, and $R_1$ to $R_8$, Y, and m are defined as defined herein.

25 Claims, No Drawings

OTHER PUBLICATIONS

Delyani, J. A. et al., "Protection from Myocardial Reperfusion Injury by Acute Administration of 17 β-Estradiol," *J. Molec. Cell. Cardiol.*, 1996, 28, 1001-1008.

Felson, D. T. et al., "The effects of estrogen on osteoarthritis,", *Curr Opinion Rheum*, 1998, 10, 269-272.

Grodstein F. et. al., "Postmenopausal Hormone Use and Secondary Prevention of Coronary Events in the Nurses' Health Study," *Ann. Int. Med*, 2001, 135, 1-8.

Grodstein, F. et. al., "A Prospective, Observational Study of Postmenopausal Hormone Therapy and Primary Prevention of Cardiovascular Disease,"*Ann. Int. Med.*, 2000, 133, 933-41.

Higuchi and Stella (eds.), *Prodrugs as Novel Drug Delivery Systems*, Ammerican Chemical Society (1975), pp. 1-115 and 196-223.

Hulley, S. et. al., "Randomized Trial of Estrogen Plus Progestin for Secondary Prevention of Coronary Heart Disease in Postmenopausal Women," *J. Am. Med. Assoc.*, 1998, 280, 605-13.

Krogsgaard-Larsen, et al., (ed). *Design and Application of Prodrugs, Textbook of Drug Design and Development*, Chapter 5, 113-191, 1991.

Kurebayashi S. et. al., "Characterization of Mechanisms of Interleukin-6 Gene Repression by Estrogen Receptor," *J. Steroid Biochem. Molec. Biol.*, 1997, 60, 11-17.

Nathan, L. et. al., "Estradiol Inhibits Leukocyte Adhesion and Transendothelial Migration in Rabbits In Vivo," *Circ. Res.*, 1999, 85, 377-385.

Pelletier et al., "Osteoarthritis, an Inflammatory Disease," *Arthr. & Rheum.*, 2001, 44:1237-1247.

Reis et. al., "Estrogen Is Associated With Improved Survival in Aging Women With Congestive Heart Failure: Analysis of the Vesnarinone Studies," *J. Am. Coll. Cardio.*, 2000, 36, 529-33.

Roth, A. et. al., "Phytoestrogen Kaempferol (3,4',5,7-Tetrahydroxylflavone) Protects PC12 and T47D Cells From β-Amyloid-Induced Toxicity," *J. Neurosci. Res.*, 1999, 57, 399-404.

Schonknecht, P. et al., "Reduced cerebrospinal fluid estradiol levels are associated with increased β-amyloid levels in female patients with Alzheimer's disease," *Neurosci. Lett.*, 2001, 307, 122-124.

Sullivan, T. R. et al. "Estrogen Inhibits the Response-to-Injury in a Mouse Carotid Artery Model," *J. Clin. Invst.*, 1995, 96, 2482-8.

Widder, et al. (ed.), *Methods in Enzymology*, vol. 112, Academic Press (1985), pp. 309-396.

Yuan et al., "Reversal of Obesity- and Diet-Induced Insulin Resistance with Salicylates or Targeted Disruption of *Ikkβ,*" *Scsience*, 2001, 293, 1673-7.

* cited by examiner

ESTROGEN RECEPTOR LIGANDS

CROSS-REFERENCE TO RELATED APPLICATION

This application claims benefit to U.S. Provisional Application No. 60/578,179, filed Jun. 9, 2004, the entirety of which is incorporated by reference herein.

FIELD OF THE INVENTION

The present invention relates to estrogen receptor ligands, and compounds and methods for treating inflammation.

BACKGROUND OF THE INVENTION

Estrogens refer to a group of hormones that play a number of well known roles in the body, including tissue and bone maintenance. Estradiol is the principal intracellular human estrogen, and is found in both women and men. Estrogen has its effect through binding of the estrogen receptor ("ER"). In endothelial cells, 17β-estradiol (E2) inhibits IL-1β induced NF-κB reporter activity and IL-6 expression in an ER dependent fashion (Kurebayashi S. et. al., *J. Steroid Biochem. Molec. Biol.*, 1997, 60, 11). This correlates with anti-inflammatory action of E2 in vivo as confirmed in different animal models of inflammation. In models of atherosclerosis, E2 was shown to protect endothelial cell integrity and function and to reduce leukocyte adhesion and intimal accumulation (Adams, M. R. et al., *Arterio.*, 1990, 1051, Sullivan, T. R. et al. *J. Clin. Invst.*, 1995, 96, 2482, Nathan, L. et. al., *Circ. Res.*, 1999, 85, 377). Similar effects of estrogen on the vascular wall have also been demonstrated in animal models of myocardial infarction (Delyani, J. A. et al., *J. Molec. Cell. Cardiol.*, 1996, 28, 1001) and congestive heart failure. Clinically, estrogen replacement therapy (ERT) has been demonstrated to reduce the risk of mortality in patients with both CHF (Reis et. al., *J. Am. Coll. Cardio.*, 2000, 36, 529) and MI (Grodstein, F. et. al., *Ann. Int. Med.*, 2000, 133, 933, Alexander et. al., *J. Am. Coll. Cardio.*, 2001, 38, 1 and Grodstein F. et. al., *Ann. Int. Med*, 2001, 135, 1). In ERT, clinical studies demonstrated an influence of E2 on the decrease in the production of β-amyloid 1-42 (Aβ42), a peptide central for the formation of senile plaques in Alzheimer's disease (Schonknecht, P. et. al., *Neurosci. Lett.*, 2001, 307, 122).

Until recently, estrogen replacement therapy was thought to be highly desirable for preventing a host of disorders, including inflammation, osteoporosis, and heart disease. However, 17-β-estradiol also strongly stimulates creatine kinase expression. Thus, in ERT some potential unwanted side effects, such as an increase risk of cardiovascular events in the first year of use, have been demonstrated (Hulley, S. et. al., *J. Am. Med. Assoc.*, 1998, 280, 605) as well as proliferative effects on uterine and breast tissue.

Therefore, ligands for the estrogen receptor are highly sought after, in order to provide the benefits noted with supplying estrogen, but without the associated risks. Estrogen receptor ligands are useful for the treatment of the inflammatory component of diseases and are particularly useful in treating atherosclerosis, myocardial infarction, congestive heart failure, inflammatory bowel disease, arthritis, type II diabetes, and autoimmune diseases such as multiple sclerosis and rheumatoid arthritis. The ability of ligands for the estrogen receptor to inhibit inflammatory gene expression causing a reduction of cytokines, chemokines, adhesion molecules and inflammatory enzymes provides a means to treat the inflammatory component of diseases such as atherosclerosis, myocardial infarction (MI), congestive heart failure (CHF), inflammatory bowel disease and arthritis. Other potential therapeutic indications for these type of molecules include type II diabetes (Cefalu, *J Womens Health & Gender-based Med.*, 2001, 10, 241 & Yuan et al., *Science*, 2001, 293, 1673), osteoarthritis (Pelletier et al., *Arthr. & Rheum.*, 2001, 44:1237 and Felson et al., *Curr Opinion Rheum*, 1998, 10, 269) asthma (Chin-Chi Lin et. al., *Immunol. Lett.*, 2000, 73, 57), Alzheimer's disease (Roth, A. et. al., *J. Neurosci. Res.*, 1999, 57, 399) and autoimmune diseases such as multiple sclerosis and rheumatoid arthritis.

A common component of these chronic inflammatory conditions is polymorphonuclear leukocyte and monocyte infiltration into the site of damage through increased expression of cytokines and adhesion molecules responsible for their recruitment. Overproduction of the cytokine interleukin (IL-6) has been associated with states of chronic inflammation (Bauer M. A., Herrmann F., *Ann. Hematol.*, 1991, 62, 203). Synthesis of the IL-6 gene is induced by the transcription factor, nuclear factor κB (NF-κB). Interference at this step in the inflammatory process can effectively regulate the uncontrolled proliferative process that occurs in these chronic conditions.

Thus, ER ligands are highly desirable for treating inflammation, and developing new ER ligands is an important undertaking.

SUMMARY OF THE INVENTION

Accordingly, in one embodiment, the present invention provides a compound of the formula I:

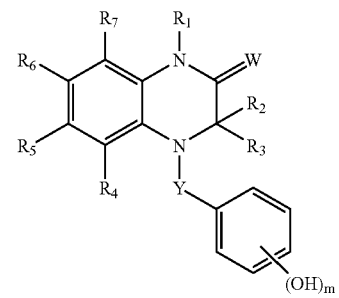

wherein:
m is 1, 2, 3, 4, or 5;
n is, independently, 0, 1, 2, 3, 4, or 5;
W is O or $C(R_8)_2$;
Y is $(C(R_8)_2)_n$—X—$(C(R_8)_2)_n$, wherein X is a bond, O, OC(=O), C(=O), or $S(O)_2$;
$R_1$ is H, C1-C6 alkyl, C2-C7 alkenyl, cycloalkyl, cycloalkenyl, or arylalkyl;
$R_2$ and $R_3$ are each, independently, H, C1-C6 alkyl, or C2-C7 alkenyl, provided that both are not H;
$R_4$, $R_5$, $R_6$, and $R_7$ are each, independently, H, C1-C6 alkyl, C2-C7 alkenyl, hydroxyl, alkoxy, aryloxy, halogen, trifluoromethyl, CN, $NO_2$, C(=O)$R_8$, or C(=O)O$R_8$; and
$R_8$ is, independently, H, C1-C6 alkyl, or phenyl.

The present invention also relates to substituted 4-(hydroxybenzoyl)-3,4-dihydroquinoxalin-2(1H)-ones and substituted 4-(hydroxyphenylsulfonyl)-3,4-dihydroquinoxalin-2(1H)-ones useful for the treatment of the inflammatory component of diseases. These compounds are particularly useful in treating atherosclerosis, myocardial infarction, congestive heart failure, inflammatory bowel disease, arthritis, type II diabetes, and autoimmune diseases such as multiple sclerosis and rheumatoid arthritis.

DETAILED DESCRIPTION OF ILLUSTRATIVE EMBODIMENTS

In one embodiment, the present invention provides a compound of the formula I:

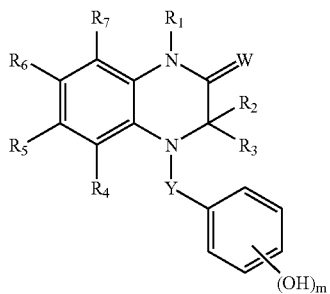

I wherein:
m is 1, 2, 3, 4, or 5;
n is, independently, 0, 1, 2, 3, 4, or 5;
W is O or $C(R_8)_2$;
Y is $(C(R_8)_2)_n$—X—$(C(R_8)_2)_n$, wherein X is a bond, O, OC(=O), C(=O), or $S(O)_2$;
$R_1$ is H, C1-C6 alkyl, C2-C7 alkenyl, cycloalkyl, cycloalkenyl, or arylalkyl;
$R_2$ and $R_3$ are each, independently, H, C1-C6 alkyl, or C2-C7 alkenyl, provided that both are not H;
$R_4$, $R_5$, $R_6$, and $R_7$ are each, independently, H, C1-C6 alkyl, C2-C7 alkenyl, hydroxyl, alkoxy, aryloxy, halogen, trifluoromethyl, CN, $NO_2$, C(=O)$R_8$, or C(=O)O$R_8$; and
$R_8$ is, independently, H, C1-C6 alkyl, or phenyl.

In one embodiment, m is 1 or 2.

In one embodiment, $R_1$ is substituted with at least one halogen.

In one embodiment, n is 0 at each occurrence, and X is C(=O), and $R_1$ is other than H or arylalkyl. Preferably, $R_1$ is C1-C6 alkyl, C2-C7 alkenyl, or cycloalkyl.

In one embodiment, n is 0 at each occurrence, and X is $S(O)_2$, and $R_1$ is C1-C6 alkyl, C2-C7 alkenyl, or arylalkyl.

In one embodiment, $R_1$ is C1-C6 alkyl or C2-C7 alkenyl.

In one embodiment, $R_2$ is C1-C6 alkyl or C2-C7 alkenyl, and $R_3$ is H. Preferably, $R_2$ is C1-C3 alkyl or C2-C4 alkenyl, and $R_3$ is H.

In one embodiment, $R_4$, $R_5$, $R_5$, and $R_7$ are each, independently, other than aryloxy, CN, $NO_2$, C(=O)$R_8$, or C(=O)O$R_8$. Preferably, $R_4$, $R_5$, $R_6$, and $R_7$ are each, independently, H, C1-C3 alkyl, C2-C4 alkenyl, halogen, or trifluoromethyl.

In one embodiment, the compound is (3R)-3-Ethyl-7-fluoro-4-(4-hydroxybenzoyl)-1-methyl-3,4-dihydroquinoxalin-2(1H)-one; (3R)-1-Benzyl-3-Ethyl-7-fluoro-4-(4-hydroxybenzoyl)-3,4-dihydroquinoxalin-2(1H)-one; (3R)-1,3-Diethyl-7-fluoro-4-(4-hydroxybenzoyl)-3,4-dihydroquinoxalin-2(1H)-one; (3R)-3-Ethyl-7-fluoro-4-(3-hydroxybenzoyl)-1-methyl-3,4-dihydroquinoxalin-2(1H)-one; (3R)-1-Benzyl-3-ethyl-7-fluoro-4-(3-hydroxybenzoyl)-3,4-dihydroquinoxalin-2(1H)-one; (3S)-1, 3-Diethyl-6-fluoro-4-(4-hydroxybenzoyl)-3,4-dihydroquinoxalin-2(1H)-one; (3S)-3-Ethyl-6-fluoro-4-(4-hydroxybenzoyl)-1-methyl-3,4-dihydroquinoxalin-2(1H)-one; (3R)-1,3-Diethyl-6-fluoro-4-(4-hydroxybenzoyl)-3,4-dihydroquinoxalin-2(1H)-one; (3R)-3-Ethyl-6-fluoro-4-(4-hydroxybenzoyl)-1-propyl-3,4-dihydroquinoxalin-2(1H)-one; (3R)-1-Allyl-3-ethyl-6-fluoro-4-(4-hydroxybenzoyl)-3, 4-dihydroquinoxalin-2(1H)-one; (3R)-3-Ethyl-6-fluoro-4-(4-hydroxybenzoyl)-1-isopropyl-3,4-dihydroquinoxalin-2 (1H)-one; (3R)-1-Butyl-3-ethyl-6-fluoro-4-(4-hydroxybenzoyl)-3,4-dihydroquinoxalin-2(1H)-one; (3R)-3-Ethyl-6-fluoro-4-(4-hydroxybenzoyl)-1-pentyl-3,4-dihydroquinoxalin-2(1H)-one; (3R)-3-Ethyl-6-fluoro-4-(4-hydroxybenzoyl)-1-isobutyl-3,4-dihydroquinoxalin-2(1H)-one; (3R)-3-Ethyl-6-fluoro-4-(4-hydroxybenzoyl)-1-methyl-3,4-dihydroquinoxalin-2(1H)-one; (3R)-3-Ethyl-6-fluoro-4-(4-hydroxybenzoyl)-1-(2,2,2-trifluoroethyl)-3,4-dihydroquinoxalin-2(1H)-one; (3R)-1-Cyclopentyl-3-ethyl-6-fluoro-4-(4-hydroxybenzoyl)-3,4-dihydroquinoxalin-2 (1H)-one; (3R)-4-(2,4-Dihydroxybenzoyl)-1,3-diethyl-6-fluoro-3,4-dihydroquinoxalin-2(1H)-one; (3R)-4-(2,4-Dihydroxybenzoyl)-3-ethyl-6-fluoro-1-methyl-3,4-dihydroquinoxalin-2(1H)-one; (3S)-3-Ethyl-6-fluoro-4-[(4-hydroxyphenyl)sulfonyl]-1-propyl-3,4-dihydroquinoxalin-2 (1H)-one; (3S)-1-Ethyl-6-fluoro-4-[(4-hydroxyphenyl)sulfonyl]-3-methyl-3,4-dihydroquinoxalin-2(1H)-one; (3S)-1-Allyl-3-ethyl-6-fluoro-4-[(4-hydroxyphenyl)sulfonyl]-3, 4-dihydroquinoxalin-2(1H)-one; (3S)-1-Butyl-3-ethyl-6-fluoro-4-[(4-hydroxyphenyl)sulfonyl]-3,4-dihydroquinoxalin-2(1H)-one; (3S)-1-benzyl-3-ethyl-6-fluoro-4-[(4-hydroxyphenyl)sulfonyl]-3,4-dihydroquinoxalin-2(1H)-one; (3S)-3-Ethyl-6-fluoro-4-[(4-hydroxyphenyl)sulfonyl]-1-methyl-3,4-dihydroquinoxalin-2(1H)-one; (3S)-1,3-Diethyl-6-fluoro-4-[(4-hydroxyphenyl)sulfonyl]-3,4-dihydroquinoxalin-2(1H)-one; (3S)-1,3-diethyl-4-[(4-hydroxyphenyl)sulfonyl]-6-methyl-3,4-dihydroquinoxalin-2(1H)-one; (3S)-3-Ethyl-4-[(4-hydroxyphenyl)sulfonyl]-1,6-dimethyl-3,4-dihydroquinoxalin-2(1H)-one; (3S)-3-Ethyl-7-fluoro-4-[(4-hydroxyphenyl)sulfonyl]-1-methyl-3,4-dihydroquinoxalin-2(1H)-one; (3S)-1,3-Diethyl-7-fluoro-4-[(4-hydroxyphenyl)sulfonyl]-3,4-dihydroquinoxalin-2(1H)-one; (3S)-7-Bromo-1,3-diethyl-4-[(4-hydroxyphenyl)sulfonyl]-3,4-dihydroquinoxalin-2(1H)-one; (3S)-7-bromo-3-ethyl-4-[(4-hydroxyphenyl)sulfonyl]-1-methyl-3,4-dihydroquinoxalin-2(1H)-one; (3S)-6-bromo-1,3-diethyl-4-[(4-hydroxyphenyl)sulfonyl]-3,4-dihydroquinoxalin-2(1H)-one; or (3S)-6-bromo-3-ethyl-4-[(4-hydroxyphenyl)sulfonyl]-1-methyl-3, 4-dihydroquinoxalin-2(1H)-one.

In one embodiment, the present invention provides a compound of the formula II:

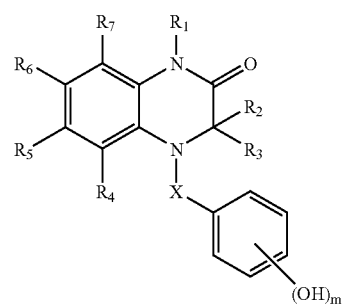

II wherein:

m is 1, 2, or 3;

X is C(=O) or S(O)$_2$;

R$_1$ is H, C1-C6 alkyl, C2-C7 alkenyl, cycloalkyl, cycloalkenyl, or arylalkyl;

R$_2$ and R$_3$ are each, independently, H, C1-C6 alkyl, C2-C7 alkenyl, provided that both are not H;

R$_4$, R$_5$, R$_6$, and R$_7$ are each, independently, H, C1-C6 alkyl, C2-C7 alkenyl, hydroxyl, alkoxy, aryloxy, halogen, trifluoromethyl, CN, NO$_2$, C(=O)R$_8$, or C(=O)OR$_8$; and R$_8$ is H, C1-C6 alkyl, or phenyl.

In one embodiment, m is 1 or 2.

In one embodiment, R$_1$ is substituted with at least one halogen.

In one embodiment, n is 0 at each occurrence, and X is C(=O), and R$_1$ is other than H or arylalkyl. Preferably, R$_1$ is C1-C6 alkyl, C2-C7 alkenyl, or cycloalkyl.

In one embodiment, n is 0 at each occurrence, and X is S(O)$_2$, and R$_1$ is C1-C6 alkyl, C2-C7 alkenyl, or arylalkyl. Preferably, R$_1$ is C1-C6 alkyl or C2-C7 alkenyl.

In one embodiment, R$_2$ is C1-C6 alkyl or C2-C7 alkenyl, and R$_3$ is H. Preferably, R$_2$ is C1-C3 alkyl or C2-C4 alkenyl, and R$_3$ is H.

In one embodiment, R$_4$, R$_5$, R$_6$, and R$_7$ are each, independently, other than aryloxy, CN, NO$_2$, C(=O)R$_8$, or C(=O)OR$_8$. Preferably, R$_4$, R$_5$, R$_6$, and R$_7$ are each, independently, H, C1-C3 alkyl, C2-C4 alkenyl, halogen, or trifluoromethyl.

In one embodiment, the present invention provides substituted 4-(hydroxybenzoyl)-3,4-dihydroquinoxalin-2(1H)-ones represented by the general formula III and substituted 4-(hydroxyphenylsulfonyl)-3,4-dihydroquinoxalin-2(1H)-ones represented by formula IV:

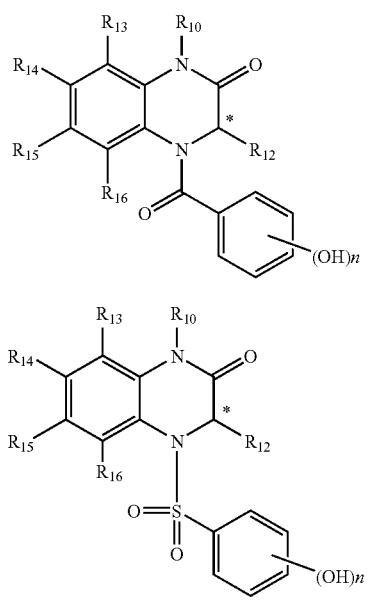

or a pharmaceutically acceptable salt thereof, wherein:

n is 1, 2, or 3;

R$_{10}$ is hydrogen, alkyl of 1-6 carbon atoms, alkenyl of 2-7 carbon atoms, cycloalkyl of 3-8 carbon atoms, cycloalkenyl of 4-8 carbon atoms, arylalkyl of 7-26 carbon atoms, all of which can be optionally substituted with 0-4 halogen groups;

R$_{12}$ is alkyl of 1-6 carbon atoms or alkenyl of 2-7 carbon atoms;

R$_{13}$, R$_{14}$, R$_{15}$ and R$_{16}$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —CN, —NO$_2$, —CHO, or —CO$_2$R$_{10}$.

The "*" indicates the R enantiomer, S enantiomer, or racemate.

Method of Using

The present invention further comprises a method for treating a patient suspected of suffering from a disease associated with excessive estrogen receptor activity, comprising the step of administering to the patient a therapeutically effective amount of a compound of formula I. In one embodiment, the disease is atherosclerosis, myocardial infarction, congestive heart failure, inflammatory bowel disease, arthritis, type II diabetes, autoimmune diseases, multiple sclerosis, or rheumatoid arthritis.

The present invention further comprises a method for modulating the activity of the estrogen receptor comprising contacting said estrogen receptor with an effective amount of a compound of formula I. The method, in one embodiment, further comprises determining the activity of said estrogen receptor. In one embodiment, said determination is made before said contacting step. In another embodiment, said determination is made after said contacting step.

Compounds of the present invention are useful for the treatment of the inflammatory component of diseases and are particularly useful in treating atherosclerosis, myocardial infarction, congestive heart failure, inflammatory bowel disease, arthritis, type II diabetes, and autoimmune diseases such as multiple sclerosis and rheumatoid arthritis.

In one embodiment, the compounds of the present invention are useful in the treatment of the inflammatory component of diseases and are therefore particularly useful in treating atherosclerosis, myocardial infarction, congestive heart failure, arthritis, inflammatory bowel disease, type II diabetes, osteoarthritis, asthma and any other autoimmune disease in humans or other mammals which comprises administering to a human or other mammal an anti-inflammatory effective amount of a compound of the present invention.

As shown in the Examples, representative compounds of this invention were evaluated in standard pharmacological test procedures which demonstrated the anti-inflammatory activity for the compounds of this invention. The test procedures used and the results obtained are briefly described in Example 35.

The ability of ligands for the estrogen receptor to inhibit inflammatory gene expression provides a means to treat the inflammatory component of diseases such as atherosclerosis, myocardial infarction (MI), congestive heart failure (CHF), inflammatory bowel disease and arthritis by causing a reduction of cytokines, chemokines, adhesion molecules and inflammatory enzymes. Other potential therapeutic indications for these type of molecules include type II diabetes (Cefalu, *J Womens Health & Gender-based Med*. 2001, 10, 241 & Yuan et al., *Science*, 2001, 293, 1673), osteoarthritis (Pelletier et al., *Arthr. & Rheum.*, 2001, 44:1237 and Felson et al., *Curr Opinion Rheum*, 1998, 10, 269) asthma (Chin-Chi Lin et. al., *Immunol. Lett.*, 2000, 73, 57), Alzheiemer's disease (Roth, A. et. al., *J. Neurosci. Res.*, 1999, 57, 399) and autoimmune diseases such as multiple sclerosis and rheumatoid arthritis.

A common component of these chronic inflammatory conditions is polymorphonuclear leukocyte and monocyte infiltration into the site of damage through increased expression of cytokines and adhesion molecules responsible for their recruitment. Overproduction of the cytokine interleukin (IL-6) has been associated with states of chronic inflammation (Bauer M. A., Herrmann F., *Ann. Hematol.*, 1991, 62, 203). Synthesis of the IL-6 gene is induced by the transcription factor nuclear factor κCB (NF-κB). Interference at this step in the inflammatory process can effectively regulate the uncontrolled proliferative process that occurs in these chronic conditions.

In endothelial cells, 17-β-estradiol (E2) inhibits IL-1β induced NF-κB reporter activity and IL-6 expression in an ER dependent fashion (Kurebayashi S. et. al., *J. Steroid Biochem. Molec. Biol.*, 1997, 60, 11). This correlates with anti-inflammatory action of E2 in vivo as confirmed in different animal models of inflammation. In models of atherosclerosis, E2 was shown to protect endothelial cell integrity and function and to reduce leukocyte adhesion and intimal accumulation (Adams, M. R. et al., *Arterio.*, 1990, 1051, Sullivan, T. R. et al. *J. Clin. Invst.* 1995, 96, 2482, Nathan, L. et. al., *Circ. Res.*, 1999, 85, 377). Similar effects of estrogen on the vascular wall have also been demonstrated in animal models of myocardial infarction (Delyani, J. A. et al., *J. Molec. Cell. Cardiol.*, 1996, 28, 1001) and congestive heart failure. Clinically, estrogen replacement therapy (ERT) has been demonstrated to reduce the risk of mortality in patients with both CHF (Reis et. al., *J. Am. Coll. Cardio.*, 2000, 36, 529) and MI (Grodstein, F. et. al., *Ann. Int. Med.*, 2000, 133, 933, Alexander et. al., *J. Am. Coll. Cardio.*, 2001, 38, 1 and Grodstein F. et. al., *Ann. Int. Med*, 2001, 135, 1). In ERT, clinical studies demonstrated an influence of E2 on the decrease in the production of β-amyloid 1-42 (Aβ42), a peptide central for the formation of senile plaques in Alzheimer's disease (Schonknecht, P. et. al., *Neurosci. Lett.*, 2001, 307, 122).

However, 17-β-estradiol also strongly stimulates creatine kinase expression. Thus, in ERT some potential unwanted side effects, such as an increase risk of cardiovascular events in the first year of use, have been demonstrated (Hulley, S. et. al., *J. Am. Med. Assoc.*, 1998, 280, 605) as well as proliferative effects on uterine and breast tissue.

Based on the results obtained in Example 35, the compounds of this invention are selective anti-inflammatory compounds useful for the treatment and prevention of chronic inflammatory diseases without stimulating uterine and breast cell proliferation as found with classic estrogens. Accordingly, the compounds of this invention are useful in treating or inhibiting osteoporosis and in the inhibition of bone demineralization, which may result from an imbalance in an individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatment or inhibition for osteoarthritis, hypocalcemia, hypercalcemia, Paget's disease, osteomalacia, osteohalisteresis, multiple myeloma and other forms of cancer having deleterious effects on bone tissues.

The compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage.

The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis, uveitis, psoriasis, multiple sclerosis, systemic lupus erythematosus and sepsis.

The compounds of this invention are also useful in treating or inhibiting ocular disorders including cataracts, uveitis, and macular degeneration and in treating skin conditions such as aging, alopecia, and acne.

The compounds of this invention are also useful in treating or inhibiting metabolic disorders such as type-II diabetes, of lipid metabolism, appetite (e.g. anorexia nervosa and bulimia).

Compounds in this invention are also useful in treating or inhibiting bleeding disorders such as hereditary hemorrhagic telangiectasia, dysfunctional uterine bleeding, and combating hemorrhagic shock.

The compounds of this invention are useful in disease states where amenorrhea is advantageous, such as leukemia, endometrial ablations, chronic renal or hepatic disease or coagulation diseases or disorders.

Methods of Making

In accordance with this invention compounds of formula III and formula IV are produced by the following reaction schemes (Schemes 1, 2, 3 and 4). Compounds can be prepared from a precursor of formula V as outlined in scheme 1.

Scheme 1

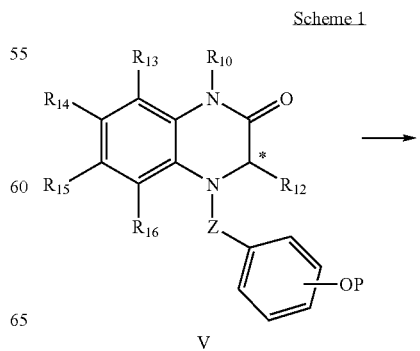

V

-continued

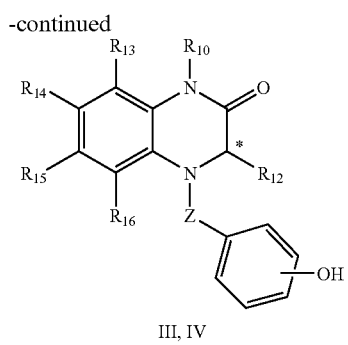

III, IV

Compounds of formula III and IV can be prepared from compounds of formula V via deprotection (Z=carbonyl or sulfonyl; P is a phenol protecting group, preferably but not limited to methyl or ethoxycarbonyl).

Where P=methyl, any conventional method for the deprotection of a methyl phenyl ether can be utilized for this conversion. In accordance with the preferred embodiment of this invention, deprotection is carried out using either $BBr_3$ with cyclohexene as a scavenger for HBr or $BCl_3$ and tetrabutylammonium iodide (Brooks, P. R., et. al.; *J. Org. Chem.* 1999, 64, 9719).

When P=ethoxycarbonyl, any conventional method for the hydrolysis of an alkyl carbonate can be utilized for this conversion. In accordance with the preferred embodiment of this invention, deprotection is performed using a nucleophilic base such as sodium hydroxide.

Scheme 2

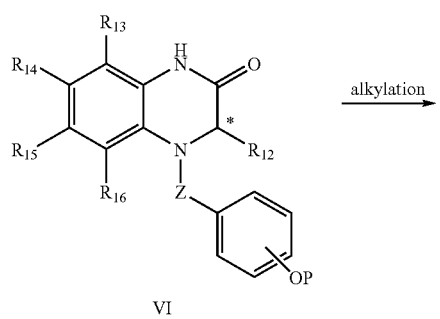

Compounds of formula V can be prepared via an alkylation reaction of the corresponding compound of formula VI. This reaction can be performed by the reaction of the compound of formula VI with an alkyl halide in the presence of a base. In accordance with the preferred embodiment of this invention, the compound of formula VI is reacted with an alkyl bromide or alkyl iodide in the presence of cesium carbonate, potassium carbonate, or a combination of the two to form the compound of formula V.

Alternatively, compounds of formula V can be prepared by the reaction of compounds of formula IV with an alcohol via activation of the alcohol to nucleophilic attack. Any conventional means for alcohol activation can be utilized in this conversion. In accordance to the preferred embodiment of this invention, the compound of formula VI is reacted, in the presence of triphenylphosphine and an alkyl azodicarboxylate, with an alcohol to form the corresponding compound of formula V.

Scheme 3

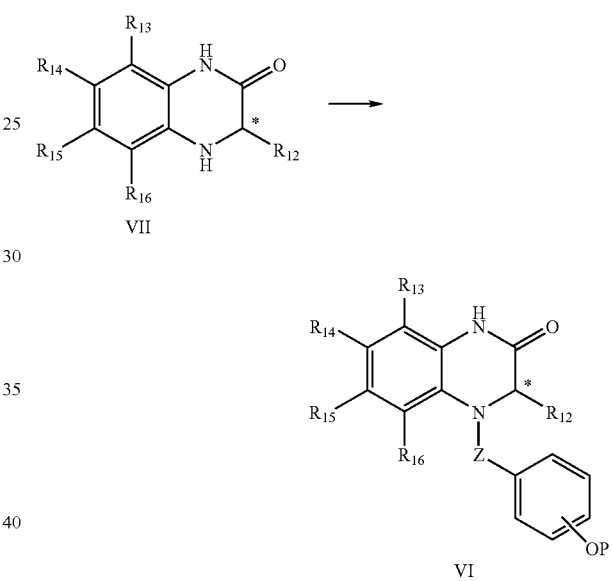

Compounds of formula VI are readily prepared from compounds of formula VII via acylation or sulfonylation. Any conventional method of acylation or sulfonylation of an aniline can be utilized to effect this conversion. In accordance with the preferred embodiment of this invention, the compound of formula VII is reacted with either an acid halide or sulfonyl halide in the presence of base, e.g. triethylamine or pyridine. A catalyst such as dimethylaminopyridine may also be used.

Scheme 4

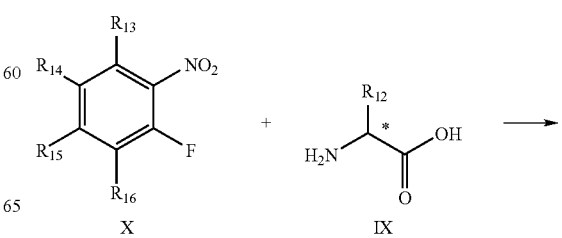

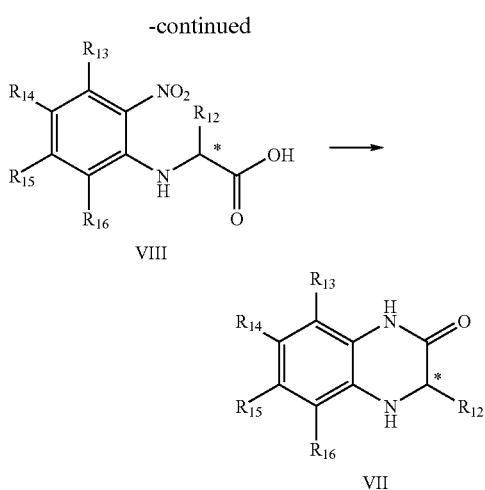

Compounds of formula VII are prepared from the nucleophilic aromatic substitution reaction of an appropriately substituted meta-fluoronitrobenzene compound of formula X with an amino acid of formula IX to form compounds of the formula VIII. Compounds of formula VIII can be readily converted to compounds of formula VII via reduction and cyclization. If it is desired to produce the R or the S isomer of the compound of formula VII, the appropriate optically pure amino acid of formula IX is chosen. The meta-fluoronitrobenzene compounds of formula X can be either commercially obtained or can be prepared by standard procedures described in the literature. Likewise, racemic, R and S amino acid compounds of formula IX can be either commercially obtained or can be prepared by standard procedures described in the literature. Any conventional method for performing nucleophilic aromatic substitution can be utilized in this conversion. In accordance with the preferred embodiment of this invention, appropriately substituted meta-fluoronitrobenzene compounds of formula X are reacted with the appropriate amino acid of formula IX, in the presence of a base such as triethylamine, at 100° C. to form compounds of formula VIII.

In the next step of the reaction, the nitro group of compounds of formula VIII is reduced and subsequently cyclized to form compounds of formula VII. Any conventional method for the reduction of a nitro group and cyclization can be employed. In accordance to the preferred embodiment of this invention, compounds of formula VIII are reduced via hydrogenation at 50 psi with 10% palladium on carbon which facilitates spontaneous cyclization to afford compounds of formula VII. In the case where $R_3$, $R_4$, $R_5$, and/or $R_6$ are groups labile to hydrogenation, such as bromo, nitro, etc. reduction and cyclization can be performed by common methods by those skilled in the art. In accordance to the preferred embodiment of this invention, compounds of formula VIII, in which $R_3$, $R_4$, $R_5$, or $R_6$ are groups labile to hydrogenation, are reduced and cyclized with iron and acetic acid at reflux which facilitates spontaneous cyclization.

Definitions

As used herein, the term "alkyl" includes both branched and straight-chain saturated aliphatic hydrocarbon groups having the specified number of carbon atoms, e.g. methyl (Me), ethyl (Et), propyl (Pr), isopropyl (i-Pr), isobutyl (i-Bu), secbutyl (s-Bu), tertbutyl (t-Bu), isopentyl, isohexyl and the like. The term "alkyl" further includes both unsubstituted and mono-, di- and tri-substituted hydrocarbon groups, with halogen substitution particularly preferred.

The term "alkenyl" refers to an unsaturated or partially unsaturated aliphatic hydrocarbon group having the specified number of carbon atoms, for example ethenyl, 1-propenyl, 2, butenyl, etc. The term "alkenyl" further includes both unsubstituted and mono-, di- and tri-substituted hydrocarbon groups, with halogen substitution particularly preferred.

The term "cycloalkyl" includes cyclized alkyl chains having the specified number of carbon atoms, e.g., cyclopropyl, cyclobutyl, cyclopentyl, and cyclohexyl. The term "cycloalkenyl" includes cyclized alkyl chains containing an alkenyl group having the specified number of carbon atoms, e.g., cyclopentenyl, cyclohexenyl, etc. The term "halogen" includes fluorine, chlorine, iodine, and bromine.

The term "aryl" means an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like.

The term "arylalkyl" means aryl, as herein before defined, suitably substituted on any open ring position with an alkyl moiety wherein the alkyl chain is either a ($C_1$-$C_6$) straight or ($C_2$-$C_7$) branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The compounds of the present invention can be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The reagents used in the preparation of the compounds of this invention can be either commercially obtained or can be prepared by standard procedures described in the literature.

The carbon number as used in the definitions herein refers to carbon backbone and carbon branching, but does not include carbon atoms of the substituents, such as alkoxy substitutions and the like.

The term "phenyl", as used herein, whether used alone or as part of another group, refers to a substituted or unsubstituted phenyl group.

An optionally substituted moiety may be substituted with one or more substituents. Suitable optionally substituents may be selected independently from H, halogen, C1-C6 alkyl, C2-C6 alkenyl, C2-C6 alkynyl, NR4R5, N[(CH2)2]2O, N[(CH2)2]2NR$_4$, NHSO2R4, NR4C(=O)R5, NHC(=O)OR4, NO2, SO2NR4R5, SO2R4, OR4, C(=O)R4, COOR4, CONR4R5, and CN.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2-difluoro ethane, 1-fluoro-2-bromo ethane, CF2CF3, CF2CF2CF3, and the like.

The term halogen includes bromine, chlorine, fluorine, and iodine.

For the sake of simplicity, connection points ("-") are not depicted. When an atom or compound is described to define a variable, it is understood that it is intended to replace the variable in a manner to satisfy the valency of the atom or compound. For example, when L is C(Rx)=C(Rx), both carbon atoms form a part of the ring in order to satisfy their respective valences.

The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "carrier", as used herein, shall encompass carriers, excipients, and diluents.

The compounds of this invention may contain an asymmetric carbon atom and some of the compounds of this invention may contain one or more asymmetric centers and may thus give rise to optical isomers and diastereomers. While shown without respect to stereochemistry in formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

The terms "effective amount", "therapeutically effective amount" and "effective dosage" as used herein, refer to the amount of a compound, that, when administered to a patient, is effective to at least partially ameliorate (and, in preferred embodiments, cure) a condition form which the patient is suspected to suffer.

Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The present invention is further described in the following examples.

EXAMPLES

Example 1

(3R)-3-Ethyl-7-fluoro-4-(4-hydroxybenzoyl)-1-methyl-3,4-dihydroquinoxalin-2(1H)-one A solution of 2,5-difluoronitrobenzene (6.29 g, 39.5 mmol) and (R)-2-aminobutyric acid (4.43 g, 43.0 mmol) and potassium carbonate (2.24 g, 16.2 mmol) in dimethylformamide (40 mL), under nitrogen, was stirred at 100° C. for 14 h. The solvent was evaporated at reduced pressure, and the residue was dissolved in 11% potassium carbonate (13.9 g in 125 mL) and washed twice with ether. Concentrated hydrochloric acid (approximately 17 mL) was added dropwise with stirring. The mixture was extracted with ethyl acetate (3×100 mL), and the extracts were washed with water (3×100 mL). The solution was dried over magnesium sulfate and the solvent was evaporated. The resulting residue crystallized upon standing to yield 7.21 g (75%) of (2R)-2-[(4-fluoro-2-nitrophenyl)amino)]-butanoic acid as reddish crystals. MS (ESI) m/z 243 ([M+H]$^+$); MS (ESI) m/z 241 ([M−H]$^−$); HRMS: calcd for $C_{10}H_{11}FN_2O_4$, 242.07031; found (ESI+), 243.07827; Anal. Calcd for $C_{10}H_{11}FN_2O_4$: C, 49.59; H, 4.58; N, 11.57. Found: C, 49.72; H, 4.49; N, 11.47.

A solution of (2R)-2-[(4-fluoro-2-nitrophenyl)amino)]-butanoic acid (9.45 g, 39.0 mmol) in ethanol (200 mL) was treated in a Parr apparatus with 10% palladium on carbon (1.50 g) and 50 psi hydrogen gas for 1.5 h, after which time hydrogen uptake had ceased. The mixture was then filtered through Celite, and the solvent was evaporated at reduced pressure. The product was purified via Biotage Horizon® (40M, silica, gradient from 15% EtOAc/hexane to 50% EtOAc/hexane) to yield 5.29 g (70%) of (3R)-3-ethyl-7-fluoro-3,4-dihydroquinoxalin-2(1H)-one as a light brown solid. MS (ESI) m/z 194 ([M+H]$^+$); MS (ESI) m/z 193 ([M−H]$^−$); HRMS: calcd for $C_{10}H_{11}FN_2O$, 194.08558; found (ESI+), 195.09281; Anal. Calcd for $C_{10}H_{11}FN_2O$: C, 61.85; H, 5.71; N, 14.42. Found: C, 61.85; H, 5.85; N, 14.46.

To a solution of (3R)-3-ethyl-7-fluoro-3,4-dihydroquinoxalin-2(1H)-one (1.3 g, 6.7 mmol) in methylene chloride (50 mL), under nitrogen was added triethylamine (1.1 mL, 0.80 g, 7.9 mmol) and 4-methoxybenzoyl chloride (0.93 mL, 1.2 g, 6.9 mmol). The solution was stirred for 16 h and was then washed successively with a 1 N aqueous solution of hydrochloric acid, a 1 N aqueous solution of sodium hydroxide, water and brine successively. The combined organic extracts were dried over magnesium sulfate and evaporated under reduced pressure to give an oil (2.2 g). The product was purified via Biotage Horizon® (SiO$_2$, gradient from 15% EtOAc/hexane to 50% EtOAc/hexane) to yield 1.4 g (64%) of (3R)-3-ethyl-7-fluoro-4-(4-methoxybenzoyl)-3,4-dihydroquinoxalin-2(1H)-one as a light tan oil. MS (ESI) m/z 329 ([M+H]$^+$); MS (ESI) m/z 327 ([M−H]$^−$); HRMS: calcd for $C18H_{17}FN_2O_3$, 328.12238; found (ESI+), 329.12930.

To a stirred solution of (3R)-3-ethyl-7-fluoro-4-(4-methoxybenzoyl)-3,4-dihydroquinoxalin-2(1H)-one (0.21 g, 0.64 mmol) in acetone (5 mL) was added potassium carbonate (0.12 g, 0.87 mmol) followed by iodomethane (0.20 mL, 0.46 g, 3.2 mmol). The reaction vessel was flushed with nitrogen and sealed. The mixture was stirred at room temperature for 16 h, after which time additional iodomethane (0.20 mL, 0.46 g, 3.2 mmol) and potassium carbonate (0.11 g, 0.80 mmol) were added. Stirring was continued at 40° C. for an additional 20 h. The solvent was then evaporated, and the resulting residue was partitioned between water and ethyl acetate, separated, washed with water and dried over magnesium sulfate. Evaporation of the solvent under reduced pressure gave (3R)-3-ethyl-7-fluoro-4-(4-methoxybenzoyl)-1-methyl-3,4-dihydroquinoxalin-2(1H)-one (quantitative) as an oil that was used without further purification. MS (ESI) m/z 343 ([M+H]$^+$); HRMS: calcd for $C_{19}H_{19}FN_2O_3$, 342.13804; found (ESI+), 343.14463.

To a stirred solution of (3R)-3-ethyl-7-fluoro-4-(4-methoxybenzoyl)-1-methyl-3,4 dihydroquinoxalin-2(1H)-one (0.19 g, 0.55 mmol) and tetrabutylammonium iodide (0.41 g, 1.1 mmol) in methylene chloride (5 mL), under nitrogen, at −78° C., was added a 1.0 M solution of boron trichloride in methylene chloride (2.8 mL, 2.8 mmol). Stirring was continued at −78° C. for 5 minutes, and the reaction was warmed to 0° C. where it was stirred for 5 h. The reaction was quenched by the addition of ice water, and the resulting mixture was stirred for 10 min. The layers were separated. The organic layer was washed with water and brine and dried over magnesium sulfate. Evaporation of the solvent and purification by eluting it through a short plug of silica gel with 75% hexane/EtOAc gave 0.16 g (88%) of (3R)-3-ethyl-7-fluoro-4-(4-hydroxybenzoyl)-1-methyl-3,4-dihydroquinoxalin-2(1H)-one. $[\alpha]_D^{25}$=−300° (c=0.009 G/ML, DMSO); MS (ESI) m/z 329 ([M+H]$^+$); MS (ESI) m/z 327 ([M−H]$^−$); HRMS: calcd for $C_{18}H_{17}FN_2O_3$, 328.1223; found (ESI+), 329.13036; Anal. Calcd for $C_{18}H_{17}FN_2O_3$: C, 65.85; H, 5.22; N, 8.53. Found: C, 65.73; H, 5.46; N, 8.28.

Example 2

(3R)-1-Benzyl-3-Ethyl-7-fluoro-4-(4-hydroxybenzoyl)-3,4-dihydroquinoxalin-2(1H)-one To a stirred solution of (3R)-3-ethyl-7-fluoro-4-(4-methoxybenzoyl)-3,4-dihydroquinoxalin-2(1H)-one (see Example 1) (0.20 g, 0.61 mmol) in acetone (10 mL) under nitrogen was added potassium carbonate (0.23 g, 17 mmol), potassium iodide (0.51 g 3.1 mmol) and benzyl bromide (0.36 mL, 0.52 g, 3.0 mmol). The mixture was heated at reflux for 2 days, after which time the acetone was evaporated. The residue was partitioned between ethyl acetate and water, and the layers were separated and washed with water. The organic layer was dried over magnesium sulfate and evaporated under reduced pressure to give a brown solid (0.60 g). The product was purified via Biotage Horizon® (SiO$_2$, gradient from 5% EtOAc/hexane to 40% EtOAc/hexane) to yield 0.19 g (74%) of (3R)-1-benzyl-3-ethyl-7-fluoro-4-(4-methoxybenzoyl)-3,4-dihydroquinoxalin-2

(1H)-one as a white solid. MS (ESI) m/z 419 ([M+H]$^+$); HRMS: calcd for $C_{25}H_{23}FN_2O_3$, 418.16936; found (ESI+), 419.17682.

To a stirred solution of (3R)-1-benzyl-3-ethyl-7-fluoro-4-(4-methoxybenzoyl)-3,4-dihydroquinoxalin-2(1H)-one (0.17 g, 0.41 mmol) and tetrabutylammonium iodide (0.28 g, 0.76 mmol) in methylene chloride (4 mL) at −78° C. was added a 1 M solution of boron trichloride in methylene chloride (2.8 mL, 2.8 mmol). Stirring was continued at −78° C. for 5 minutes, and the reaction was warmed to 0° C., where it was stirred for 10 h. Ice water was then added and stirred thoroughly. The layers were separated. The organic layer was washed with water and brine and dried over magnesium sulfate. Evaporation of the solvent under reduced pressure gave an oil (0.26 g). The product was purified via Biotage Horizon® (SiO$_2$, gradient from 5% EtOAc/hexane to 35% EtOAc/hexane) to quantitatively yield (3R)-1-benzyl-3-ethyl-7-fluoro-4-(4-hydroxybenzoyl)-3,4-dihydroquinoxalin-2(1H)-one as a colorless oil. $[\alpha]_D^{25}$=250° (c=0.0097 G/ML, CHCl$_3$); MS (ESI) m/z 405 ([M+H]$^+$); MS (ESI) m/z 403 ([M−H]$^−$); HRMS: calcd for $C_{24}H_{21}FN_2O_3$ 0.67H$_2$O, 416.2207; found (ESI+), 405.16006.

Example 3

(3R)-1,3-Diethyl-7-fluoro-4-(4-hydroxybenzoyl)-3,4-dihydroquinoxalin-2(1H)-one

To a stirred solution of (3R)-3-ethyl-7-fluoro-4-(4-methoxybenzoyl)-3,4-dihydroquinoxalin-2(1H)-one (see Example 1) (0.20 g, 0.61 mmol) in acetone (5 mL) under nitrogen was added potassium carbonate (0.23 g, 17 mmol) and iodoethane (0.35 mL, 0.68 g, 4.4 mmol). The mixture was heated at reflux for 3.5 days. Cesium carbonate (0.10 g, 0.31 mmol) was added, and the mixture was heated at reflux for an additional 3 h. The acetone was then evaporated, and the residue was partitioned between ethyl acetate and water. The layers were separated and the organic layer was washed with water. The combined organic extracts were dried over magnesium sulfate and evaporated under reduced pressure to give an oil (0.21 g). The product was purified via Biotage Horizon® (SiO$_2$, gradient from 5% EtOAc/hexane to 35% EtOAc/hexane) to yield 0.19 g (87%) of (3R)-1,3-diethyl-7-fluoro-4-(4-methoxybenzoyl)-3,4-dihydroquinoxalin-2(1H)-one as an oil. MS (ESI) m/z 357 ([M+H]$^+$); HRMS: calcd for $C_{20}H_{21}FN_2O_3$, 356.1537; found (ESI+), 357.16135.

To a stirred solution of (3R)-1,3-diethyl-7-fluoro-4-(4-methoxybenzoyl)-3,4-dihydroquinoxalin-2(1H)-one (0.13 g, 0.36 mmol) and tetrabutylammonium iodide (0.26 g, 0.70 mmol) in methylene chloride (3.6 mL) at −78° C. was added a 1 M solution of boron trichloride in methylene chloride (2.8 mL, 2.8 mmol). Stirring was continued at −78° C. for 5 minutes, and the reaction was warmed to 0° C. where it was stirred for 3 h. Ice water was then added and the resulting mixture was stirred for 30 minutes. The layers were separated. The organic layer was washed with water and dried over magnesium sulfate. Evaporation of the solvent under reduced pressure gave an oil (0.39 g). The product was purified via Biotage Horizon® (SiO$_2$, gradient from 5% EtOAc/hexane to 40% EtOAc/hexane) to yield 0.11 g (89%) of (3R)-1,3-diethyl-7-fluoro-4-(4-hydroxybenzoyl)-3,4-dihydroquinoxalin-2(1H)-one as a colorless oil. $[\alpha]_D^{25}$=−248° (c=0.0096 G/ML, CHCl$_3$); MS (ESI) m/z 343 ([M+H]$^+$); MS (ESI) m/z 341 ([M−H]$^−$); HRMS: calcd for $C_{19}H_{19}FN_2O_3$.0.10H$_2$O, 343.9390; found (ESI+), 343.14456, Anal. Calcd for $C_{19}H_{19}FN_2O_3$.0.10H$_2$O: C, 66.31; H, 5.62; N, 8.14. Found: C, 66.05; H, 5.36; N, 8.02.

Example 4

(3R)-3-Ethyl-7-fluoro-4-(3-hydroxybenzoyl)-1-methyl-3,4-dihydroquinoxalin-2(1H)-one (3R)-3-Ethyl-7-fluoro-3,4-dihydroquinoxalin-2(1H)-one (see Example 1) was treated with 3-methoxybenzoyl chloride according to the procedure for the preparation of (3R)-3-ethyl-7-fluoro-4-(4-methoxybenzoyl)-3,4-dihydroquinoxalin-2(1H)-one (see Example 1) to yield (3R)-3-ethyl-7-fluoro-4-(3-methoxybenzoyl)-3,4-dihydroquinoxalin-2(1H)-one (76%). MS (ESI) m/z 329 ([M+H]$^+$); MS (ESI) m/z 327 ([M−H]$^−$); HRMS: calcd for $C_{18}H_{17}FN_2O_3$, 328.12238; found (ESI+), 329.12924.

To a stirred solution of (3R)-3-ethyl-7-fluoro-4-(3-methoxybenzoyl)-3,4-dihydroquinoxalin-2(1H)-one (0.25 g, 0.76 mmol) in acetone (5 mL), under nitrogen was added potassium carbonate (0.07 g, 0.5 mmol), cesium carbonate (0.18 g, 0.55 mmol) and iodomethane (0.34 mL, 0.78 g, 5.5 mmol). The reaction was stirred at 52° C. for 16 h. The solvent was evaporated. The residue was partitioned between water and ethyl acetate, and the layers were separated. The organic layer was washed with water and dried over magnesium sulfate. Evaporation of the solvent in vacuo quantitatively gave (3R)-3-ethyl-7-fluoro-4-(3-methoxybenzoyl)-1-methyl-3,4-dihydroquinoxalin-2(1H)-one.

(3R)-3-Ethyl-7-fluoro-4-(3-methoxybenzoyl)-1-methyl-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2 (1H)-one (see Example 1) to give an oil which was purified via Biotage Horizon® (SiO$_2$, gradient from 5% EtOAc/hexane to 40% EtOAc/hexane) to yield (3R)-3-ethyl-7-fluoro-4-(3-hydroxybenzoyl)-1-methyl-3,4-dihydroquinoxalin-2(1H)-one (72%). $[\alpha]_D^{25}$=−281° (c=0.0098 G/ML, CHCl$_3$); MS (ESI) m/z 329 ([M+H]$^+$); MS (ESI) m/z 327 ([M−H]$^−$) HRMS: calcd for $C_{18}H_{17}FN_2O_3$.0.10H$_2$O, 329.9234; found (ESI+), 329.12884; Anal. Calcd for C18H$_{17}$FN$_2$O$_3$ 0.10H$_2$O: C, 65.49; H, 5.25; N, 8.49. Found: C, 65.29; H, 4.93; N, 8.33.

Example 5

(3R)-1-Benzyl-3-ethyl-7-fluoro-4-(3-hydroxybenzoyl)-3,4-dihydroquinoxalin-2(1H)-one (3R)-3-Ethyl-7-fluoro-4-(3-methoxybenzoyl)-3,4-dihydroquinoxalin-2(1H)-one (see Example 4) was treated with potassium iodide (5 eq) and benzyl bromide according to the procedure for the preparation of (3R)-1-benzyl-3-ethyl-7-fluoro-4-(4-methoxybenzoyl)-3,4-dihydroquinoxalin-2 (1H)-one (see Example 2) to yield (3R)-1-benzyl-3-ethyl-7-fluoro-4-(3-methoxybenzoyl)-3,4-dihydroquinoxalin-2 (1H)-one (85%).

(3R)-1-Benzyl-3-ethyl-7-fluoro-4-(3-methoxybenzoyl)-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2 (1H)-one (see Example 1) to yield (3R)-1benzyl-3-ethyl-7-fluoro-4-(3-hydroxybenzoyl)-3,4-dihydroquinoxalin-2(1H)-one (74%). $[\alpha]_D^{25}$=−279° (c=0.0095G/ML, CHCl$_3$); MS (ESI) m/z 405 ([M+H]$^+$); MS (ESI) m/z 403 ([M−H]$^−$); HRMS: calcd for $C_{24}H_{21}FN_2O_3$.0.25H$_2$O, 408.6563; found (ESI+), 405.16003; Anal. Calcd for C24H21FN2O3.0.25H2O: C, 70.49; H, 5.30; N, 6.85. Found: C, 70.42; H, 5.19; N, 6.75.

Example 6

(3S)-1,3-Diethyl-6-fluoro-4-(4-hydroxybenzoyl)-3,4-dihydroquinoxalin-2(1H)-one

A solution of 2,4-difluoronitrobenzene (7.75 g, 48.7 mmol), (S)-2-aminobutyric acid (5.5 g, 53.3 mmol) and potassium carbonate (2.77 g, 20.0 mmol) in dimethylformamide (40 mL), under nitrogen, was stirred at 110° C. for 14 h. The solvent was evaporated in vacuo, and the residue was dissolved in 11% potassium carbonate (13.9 g in 125 mL) and washed twice with ether. Concentrated hydrochloric acid (approximately 20 mL) was added dropwise with stirring. The mixture was extracted with ethyl acetate (3×100 mL), and the extracts were washed with water (3×100 mL). The solution was dried over magnesium sulfate and the solvent was evaporated. The resulting residue crystallized upon standing to yield 7.5 g (63%) of (2S)-2-[(5-fluoro-2-nitrophenyl)amino)]-butanoic acid as a dark orange oil. MS (ESI) m/z [M–H]–=(241).

A solution of (2S)-2-[(5-fluoro-2-nitrophenyl)amino)]-butanoic acid (7.5 g, 31.0 mmol) in ethanol (200 mL) was treated in a Parr apparatus with 10% palladium on carbon (1.50 g) and 50 psi hydrogen gas for 1.5 h, after which time hydrogen uptake had ceased. The mixture was then filtered through Celite, and the solvent was evaporated at reduced pressure. The product was purified via Biotage Horizon® (40M, $SiO_2$, gradient from 15% EtOAc/hexane to 50% EtOAc/hexane) to yield 6.0 g (quantitative) of (3S)-3-ethyl-6-fluoro-3,4-dihydroquinoxalin-2(1H)-one as a white solid. $[\alpha]_D^{25}$=+18.61° (c=0.010 G/ML, DMSO); MS (ESI) m/z 195 ([M+H]$^+$); Anal. Calcd for $C_{10}H_{11}FN_2O$: C, 61.85; H, 5.71; N, 14.42. Found: C, 61.72; H, 5.80; N, 14.33.

(3S)-3-Ethyl-6-fluoro-3,4-dihydroquinoxalin-2(1H)-one in ether was treated according to the procedure for the preparation of (3R)-3-ethyl-7-fluoro-4-(4-methoxybenzoyl)-3,4-dihydroquinoxalin-2(1H)-one (see Example 1) to yield (3S)-3-ethyl-6-fluoro-4-(4-methoxybenzoyl)-3,4-dihydroquinoxalin-2(1H)-one (82%). MS (ESI) m/z 329 ([M+H]$^+$); MS (ESI) m/z 327 ([M–H]$^-$).

To a stirred solution of (3S)-3-ethyl-6-fluoro-4-(4-methoxybenzoyl)-3,4-dihydroquinoxalin-2(1H)-one (0.25 g, 0.76 mmol) in acetone (6 mL) under nitrogen was added cesium carbonate (0.133 g, 0.41 mmol), potassium carbonate (0.057 g, 0.41 mmol) and iodoethane (0.20 mL, 0.39 g, 2.5 mmol). The reaction was stirred at 51° C. for 4 h. The solvent was evaporated, and the residue was partitioned between methylene chloride and water. The organic layer was separated and washed with water. The combined organic layers were dried over magnesium sulfate and concentrated in vacuo. The product was purified via Biotage Horizon® ($SiO_2$, gradient from 4% EtOAc/hexane to 38% EtOAc/hexane) to yield 0.19 g (75%) of (3S)-1,3-diethyl-6-fluoro-4-(4-methoxybenzoyl)-3,4-dihydroquinoxalin-2(1H)-one. MS (ESI) m/z 357 ([M+H]$^+$).

(3S)-1,3-Diethyl-6-fluoro-4-(4-methoxybenzoyl)-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3S)-1,3-diethyl-6-fluoro-4-(4-hydroxybenzoyl)-3,4-dihydroquinoxalin-2(1H)-one (93%). $[\alpha]_D^{25}$=+295° (c=0.0098 G/ML, CHCl$_3$); MS (ESI) m/z 343 ([M+H]$^+$); MS (ESI) m/z 341 ([M–H]$^-$); HRMS: calcd for $C_{19}H_{19}FN_2O_3$, 342.1380; found (ESI_FT), 343.14475.

Example 7

(3S)-3-Ethyl-6-fluoro-4-(4-hydroxybenzoyl)-1-methyl-3,4-dihydroquinoxalin-2(1H)-one (3S)-3-Ethyl-6-fluoro-4-(4-methoxybenzoyl)-3,4-dihydroquinoxalin-2(1H)-one (see Example 6) was treated according to the procedure for the preparation of (3R)-3-ethyl-7-fluoro-4-(4-methoxybenzoyl)-1-methyl-3,4-dihydroquinoxalin-2(1H)-one (see Example 1) to yield (3S)-3-ethyl-6-fluoro-4-(4-methoxybenzoyl)-1-methyl-3,4-dihydroquinoxalin-2(1H)-one (83%).

(3S)-3-Ethyl-6-fluoro-4-(4-methoxybenzoyl)-1-methyl-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3S)-3-Ethyl-6-fluoro-4-(4-hydroxybenzoyl)-1-methyl-3,4-dihydroquinoxalin-2(1H)-one (87%). $[\alpha]_D^{25}$=+301° (c=0.0107 G/ML, CHCl$_3$); MS (ESI) m/z 329 ([M+H]$^+$); MS (ESI) m/z 327 ([M–H]$^-$); HRMS: calcd for $C_{18}H_{17}FN_2O_3$, 328.1223; found (ESI_FT), 329.12904;

Example 8

(3R)-1,3-Diethyl-6-fluoro-4-(4-hydroxybenzoyl)-3,4-dihydroquinoxalin-2(1H)-one 2,4-Difluoronitrobenzene was treated according to the procedure for the preparation of (R)-2-(4-fluoro-2-nitrophenylamino)-butyric acid (see Example 1) to yield (R)-2-(5-fluoro-2-nitrophenylamino)-butyric acid (83%). MS (ESI) m/z 243 ([M#H]$^+$); MS (ESI) m/z 241 ([M–H]$^-$); HRMS: calcd for $C_{10}H_{11}FN_2O_4$, 242.07031; found (ESI+), 243.07712.

(2R)-2-(5-Fluoro-2-nitrophenylamino)-butyric acid was treated according to the procedure for the preparation of (3R)-3-ethyl-7-fluoro-3,4-dihydroquinoxalin-2(1H)-one (see Example 1) to yield (3R)-3-ethyl-6-fluoro-3,4-dihydroquinoxalin-2(1H)-one (54%). MS (ESI) m/z 195 ([M+H]$^+$); HRMS: calcd for $C_{10}H_{11}FN_2O$, 194.08558; found (ESI_FT), 195.08807; Anal. Calcd for $C_{10}H_{11}FN_2O$: C, 61.85; H, 5.71; N, 14.42. Found: C, 61.77; H, 5.76; N, 14.33.

(3R)-3-Ethyl-6-fluoro-3,4-dihydroquinoxalin-2(1H)-one in ether was treated according to the procedure for the preparation of (3R)-3-ethyl-7-fluoro-4-(4-methoxybenzoyl)-3,4-dihydroquinoxalin-2(1H)-one (see Example 1) to yield (3R)-3-ethyl-6-fluoro-4-(4-methoxybenzoyl)-3,4-dihydroquinoxalin-2(1H)-one (76%). MS (ESI) m/z 329 ([M+H]$^+$); MS (ESI) m/z 327 ([M–H]$^-$); HRMS: calcd for $C_{18}H_{17}FN_2O_3$, 328.12238; found (ESI_FT), 329.12878.

To a stirred solution of (3R)-3-ethyl-6-fluoro-4-(4-methoxybenzoyl)-3,4-dihydroquinoxalin-2(1H)-one (0.20 g, 0.61 mmol) in acetonitrile (5 mL) under nitrogen was added potassium carbonate (0.050 g, 0.36 mmol), cesium carbonate (0.11 g, 0.33 mmol) and iodoethane (0.15 mL, 0.29 g, 1.9 mmol). The reaction was stirred for 10 h at 50° C. and then 5 h at 63° C. The solvent was evaporated, and the residue was partitioned between ethyl acetate and water. The layers were separated and the organic layer was washed with water. The organic layer was concentrated in vacuo and purified via Biotage Horizon® ($SiO_2$, gradient from 5% EtOAc/hexane to 33% EtOAc/hexane) to yield 0.21 g (96%) of (3R)-1,3- diethyl-6-fluoro-4-(4-methoxybenzoyl)-3,4-dihydroquinoxalin-2(1H)-one. MS (ESI) m/z 357 ([M+H]$^+$); HRMS: calcd for $C_{20}H_{21}FN_2O_3$, 356.16090; found (ESI+), 357.16057.

(3R)-1,3-Diethyl-6-fluoro-4-(4-methoxybenzoyl)-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-1,3-diethyl-6-fluoro-4-(4-hydroxybenzoyl)-3,4-dihydroquinoxalin-2(1H)-one (83%). $[\alpha]_D^{25}=-300°$ (c=0.010 G/ML, CHCl$_3$); MS (ESI) m/z 343 ([M+H]$^+$); MS (ESI) m/z 341 ([M−H]$^−$); HRMS: calcd for $C_{19}H_{19}FN_2O_3$, 342.1380; found (ESI_FT), 343.14482.

Example 9

(3R)-3-Ethyl-6-fluoro-4-(4-hydroxybenzoyl)-1-propyl-3,4-dihydroquinoxalin-2(1H)-one (3R)-3-Ethyl-6-fluoro-4-(4-methoxybenzoyl)-3,4-dihydroquinoxalin-2(1H)-one (see Example 8) was treated with allyl bromide according to the procedure for the preparation of (3R)-3-ethyl-7-fluoro-4-(4-methoxybenzoyl)-1-methyl-3,4-dihydroquinoxalin-2(1H)-one (see Example 1) to yield (3R)-1-allyl-3-ethyl-6-fluoro-4-(4-methoxybenzoyl)-3,4-dihydroquinoxalin-2(1H)-one (81%). MS (ESI) m/z 369 ([M+H]$^+$); HRMS: calcd for $C_{21}H_{21}FN_2O_3$, 368.1537; found (ESI+), 369.16115.

(3R)-1-Allyl-3-ethyl-6-fluoro-4-(4-methoxybenzoyl)-3,4-dihydroquinoxalin-2(1H)-one was treated according to the procedure for the preparation of (3R)-3-ethyl-7-fluoro-3,4-dihydroquinoxalin-2(1H)-one (see Example 1) to quantitatively yield (3R)-3-ethyl-6-fluoro-4-(4-methoxybenzoyl)-1-propyl-3,4-dihydroquinoxalin-2(1H)-one. MS (ESI) m/z 371 ([M+H]$^+$).

(3R)-3-Ethyl-6-fluoro-4-(4-methoxybenzoyl)-1-propyl-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-3-ethyl-6-fluoro-4-(4-hydroxybenzoyl)-1-propyl-3,4-dihydroquinoxalin-2(1H)-one (81%). $[\alpha]_D^{25}=-298°$ (c=0.0102 G/ML, CHCl$_3$); MS (ESI) m/z 357 ([M+H]$^+$); MS (ESI) m/z 355 ([M−H]$^−$); HRMS: calcd for $C_{20}H_{21}FN_2O_3$, 356.1536; found (ESI_FT), 357.16057.

Example 10

(3R)-1-Allyl-3-ethyl-6-fluoro-4-(4-hydroxybenzoyl)-3,4-dihydroquinoxalin-2(1H)-one (3R)-1-Allyl-3-ethyl-6-fluoro-4-(4-methoxybenzoyl)-3,4-dihydroquinoxalin-2(1H)-one (see Example 9) was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-1-allyl-3-ethyl-6-fluoro-4-(4-hydroxybenzoyl)-3,4-dihydroquinoxalin-2(1H)-one (97%). $[\alpha]_D^{25}=-285°$ (c=0.0102 G/ML, CHCl$_3$); MS (ESI) m/z 355 ([M+H]$^+$); MS (ESI) m/z 353 ([M−H]$^−$); HRMS: calcd for $C_{20}H_{19}FN_2O_3$, 354.1380; found (ESI_FT), 355.1449.

Example 11

(3R)-3-Ethyl-6-fluoro-4-(4-hydroxybenzoyl)-1-isopropyl-3,4-dihydroquinoxalin-2(1H)-one (3R)-3-Ethyl-6-fluoro-4-(4-methoxybenzoyl)-3,4-dihydroquinoxalin-2(1H)-one (see Example 8) was treated with isopropyl iodide at reflux according to the procedure for the preparation of (3R)-1,3-diethyl-6-fluoro-4-(3-methoxybenzoyl)-3,4-dihydroquinoxalin-2(1H)-one (see Example 8) to yield (3R)-3-ethyl-6-fluoro-4-(4-methoxybenzoyl)-1-isopropyl-3,4-dihydroquinoxalin-2(1H)-one (54%). MS (ESI) m/z 371 ([M+H]$^+$).

(3R)-3-Ethyl-6-fluoro-4-(4-methoxybenzoyl)-1-isopropyl-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-3-ethyl-6-fluoro-4-(4-hydroxybenzoyl)-1-isopropyl-3,4-dihydroquinoxalin-2(1H)-one (92%). $[\alpha]_D^{25}=-309°$ (c=0.0099 G/ML, CHCl$_3$); MS (ESI) m/z 357 ([M+H]$^+$); MS (ESI) m/z 355 ([M−H]$^−$); HRMS: calcd for $C_{20}H_{21}FN_2O_3$, 356.1536; found (ESI_FT), 357.16064.

Example 12

(3R)-1-Butyl-3-ethyl-6-fluoro-4-(4-hydroxybenzoyl)-3,4-dihydroquinoxalin-2(1H)-one (3R)-3-Ethyl-6-fluoro-4-(4-methoxybenzoyl)-3,4-dihydroquinoxalin-2(1H)-one (see Example 8) was treated with 1-bromobutane according to the procedure for the preparation of (3R)-3-ethyl-7-fluoro-4-(3-methoxybenzoyl)-1-methyl-3,4-dihydroquinoxalin-2(1H)-one (see Example 4) to yield (3R)-1-butyl-3-ethyl-6-fluoro-4-(4-methoxybenzoyl)-3,4-dihydroquinoxalin-2(1H)-one (76%). MS (ESI) m/z 385 ([M+H]$^+$).

(3R)-1-Butyl-3-ethyl-6-fluoro-4-(4-methoxybenzoyl)-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-1-butyl-3-ethyl-6-fluoro-4-(4-hydroxybenzoyl)-3,4-dihydroquinoxalin-2(1H)-one (94%). $[\alpha]_D^{25}=-268°$ (c=0.0103G/ML, CHCl$_3$); MS (ESI) m/z 371 ([M+H]$^+$); MS (ESI) m/z 369 ([M−H]$^−$); HRMS: calcd for $C_{21}H_{23}FN_2O_3$, 370.1693; found (ESI_FT), 371.17594; Anal. Calcd for $C_{21}H_{23}FN_2O_3$: C, 68.09; H, 6.26; N, 7.56. Found: C, 67.96; H, 6.60; N, 7.67.

Example 13

(3R)-3-Ethyl-6-fluoro-4-(4-hydroxybenzoyl)-1-pentyl-3,4-dihydroquinoxalin-2(1H)-one (3R)-3-Ethyl-6-fluoro-4-(4-methoxybenzoyl)-3,4-dihydroquinoxalin-2(1H)-one (see Example 8) was treated with 1-bromopentane and potassium iodide (1.2 eq) according to the procedure for the preparation of (3R)-3-ethyl-7-fluoro-4-(3-methoxybenzoyl)-1-methyl-3,4-dihydroquinoxalin-2(1H)-one (see Example 4) to yield (3R)-3-ethyl-6-fluoro-4-(4-methoxybenzoyl)-1-pentyl-3,4-dihydroquinoxalin-2(1H)-one (55%). MS (ESI) m/z 399 ([M+H]$^+$).

(3R)-3-Ethyl-6-fluoro-4-(4-methoxybenzoyl)-1-pentyl-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-3-ethyl-6-fluoro-4-(4- hydroxybenzoyl)-1-pentyl-3,4-dihydroquinoxalin-2(1H)-one (96%). [α]D $^{25}$=−294° (c=0.0095 G/ML, CHCl$_3$); MS (ESI) m/z 385 ([M+H]$^+$); MS (ESI) m/z 383 ([M−H]$^−$); HRMS: calcd for C$_{22}$H$_{25}$FN$_2$O$_3$.0.10H$_2$O, 385.9860; found (ESI_FT), 385.19204.

Example 14

(3R)-3-Ethyl-6-fluoro-4-(4-hydroxybenzoyl)-1-isobutyl-3,4-dihydroquinoxalin-2(1H)-one To a stirred solution of (3R)-3-ethyl-6-fluoro-4-(4-methoxybenzoyl)-3,4-dihydroquinoxalin-2(1H)-one (see Example 8) (0.25 g, 0.76 mmol) in acetonitrile (6 mL) under nitrogen was added cesium carbonate (0.13 g, 0.40 mmol), potassium carbonate (0.055 g, 0.40 mmol) and 1-iodo-2-methylpropane (0.30 mL, 0.48 g, 2.6 mmol). The mixture was stirred at 74° C. for 12 h. The solvent was then evaporated, and the residue was partitioned between methylene chloride and water. The organic layer was separated, washed with water, dried over magnesium sulfate, and concentrated in vacuo. The product was purified via Biotage Horizon® (SiO$_2$, gradient from 4% EtOAc/hexane to 38% EtOAc/hexane) to yield 0.10 g (35%) of (3R)-3-ethyl-6-fluoro-4-(4-methoxybenzoyl)-1-isobutyl-3,4-dihydroquinoxalin-2(1H)-one.

(3R)-3-Ethyl-6-fluoro-4-(4-methoxybenzoyl)-1-isobutyl-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-3-ethyl-6-fluoro-4-(4-hydroxybenzoyl)-1-isobutyl-3,4-dihydroquinoxalin-2(1H)-one (93%). [α]$_D^{25}$=−272° (c=0.010 G/ML, CHCl$_3$); MS (ESI) m/z 371 ([M+H]$^+$); MS (ESI) m/z 369 ([M−H]$^−$); HRMS: calcd for C$_{21}$H$_{23}$FN$_2$O$_3$, 370.1693; found (ESI_FT), 371.17594; Anal. Calcd for C$_{21}$H$_{23}$FN$_2$O$_3$: C, 68.09; H, 6.26; N, 7.56. Found: C, 67.85; H, 6.24; N, 7.65.

Example 15

(3R)-3-Ethyl-6-fluoro-4-(4-hydroxybenzoyl)-1-methyl-3,4-dihydroquinoxalin-2(1H)-one (3R)-3-Ethyl-6-fluoro-4-(4-methoxybenzoyl)-3,4-dihydroquinoxalin-2(1H)-one (see Example 8) was treated according to the procedure for the preparation of (3R)-3-ethyl-7-fluoro-4-(3-methoxybenzoyl)-1-methyl-3,4-dihydroquinoxalin-2(1H)-one (see Example 4) to yield (3R)-3-ethyl-6-fluoro-4-(4-methoxybenzoyl)-1-methyl-3,4-dihydroquinoxalin-2(1H)-one (76%). MS (ESI) m/z 343 ([M+H]$^+$); HRMS: calcd for C$_{19}$H$_{19}$FN$_2$O$_3$, 342.13804; found (ESI+), 343.14480.

(3R)-3-Ethyl-6-fluoro-4-(4-methoxybenzoyl)-1-methyl-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-3-ethyl-6-fluoro-4-(4-hydroxybenzoyl)-1-methyl-3,4-dihydroquinoxalin-2(1H)-one (71%). [α]$_D^{25}$=−290° (c=0.0095 G/ML, CHCl$_3$); MS (ESI) m/z 329 ([M+H]$^+$); MS (ESI) m/z 327 ([M−H]$^−$); HRMS: calcd for C$_{18}$H$_{17}$FN$_2$O$_3$, 328.1223; found (ESI_FT), 329.12887.

Example 16

(3R)-3-Ethyl-6-fluoro-4-(4-hydroxybenzoyl)-1-(2,2,2-trifluoroethyl)-3,4-dihydroquinoxalin-2(1H)-one (3R)-3-Ethyl-6-fluoro-4-(4-methoxybenzoyl)-3,4-dihydroquinoxalin-2(1)-one (see Example 8) was treated at 84° C. in a sealed tube according to the procedure for the preparation of (3R)-3-ethyl-6-fluoro-4-(4-methoxybenzoyl)-1-isobutyl-3,4-dihydroquinoxalin-2(1H)-one see Example 14) to yield (3R)-3-ethyl-6-fluoro-4-(4-methoxybenzoyl)-1-(2,2,2-trifluoroethyl)-3,4-dihydroquinoxalin-2(1H)-one (60%). MS (ESI) m/z 411 ([M+H]$^+$).

(3R)-3-Ethyl-6-fluoro-4-(4-methoxybenzoyl)-1-(2,2,2-trifluoroethyl)-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-3-ethyl-6-fluoro-4-(4-hydroxybenzoyl)-1-(2,2,2-trifluoroethyl)-3,4-dihydroquinoxalin-2(1H)-one (73%). [α]$_D^{25}$=−137° (c=0.010 G/ML, CHCl$_3$); MS (ESI) m/z 397 ([M+H]$^+$); MS (ESI) m/z 395 ([M−H]$^−$); HRMS: calcd for C$_{19}$H$_{16}$F$_4$N$_2$O$_3$, 396.1097; found (ESI_FT), 397.11588.

Example 17

(3R)-1-Cyclopentyl-3-ethyl-6-fluoro-4-(4-hydroxybenzoyl)-3,4-dihydroquinoxalin-2(1H)-one To a stirred solution of (3R)-3-ethyl-6-fluoro-4-(4-methoxybenzoyl)-3,4-dihydroquinoxalin-2(1H)-one (see Example 8) (0.47 g, 1.4 mmol) in tetrahydrofuran (4 mL) under nitrogen at 0° C. was added cyclopentanol (0.20 mL, 0.19 g, 2.2 mmol), triphenylphosphine (0.58 g, 2.2 mmol), and diethyl azodicaboxylate (0.44 mL, 0.46 g, 0.22 mmol). The reaction was warmed to 25° C. and was stirred for 12 h. The solvent was evaporated in vacuo, and the product was purified via Biotage Horizon® (SiO$_2$, gradient from 5% EtOAc/hexane to 40% EtOAc/hexane) to yield 0.20 g (36%) of (3R)-1-cyclopentyl-3-ethyl-6-fluoro-4-(4-methoxybenzoyl)-3,4-dihydroquinoxalin-2(1H)-one. MS (ESI) m/z 397 ([M+H]$^+$).

(3R)-1-Cyclopentyl-3-ethyl-6-fluoro-4-(4-methoxybenzoyl)-3,4-dihydroquinoxalin-2(1H)-one was treated according to the procedure for the preparation of (3R)-3-ethyl-7-fluoro-4(4-hydroxybenzoyl)-1-methyl-3,4-dihydroquinoxalin-2(1H)-one (see Example 1) to yield (3R)-1-cyclopentyl-3-ethyl-6-fluoro-4-(4-hydroxybenzoyl)-3,4-dihydroquinoxalin-2(1H)-one (40%). [α]$_D^{25}$=−309° (c=0.0095 G/ML, CHCl$_3$); MS (ESI) m/z 383 ([M+H]$^+$); MS (ESI) m/z 381 ([M−H]$^−$); HRMS: calcd for C$_{22}$H$_{23}$FN$_2$O$_3$, 382.1693; found (ESI_FT), 383.17555.

Example 18

(3R)-4-(2,4-Dihydroxybenzoyl)-1,3-diethyl-6-fluoro-3,4-dihydroquinoxalin-2(1H)-one (3R)-3-Ethyl-6-fluoro-3,4-dihydroquinoxalin-2(1H)-one (see Example 8) was treated with 2,4-dimethoxybenzoyl chloride in the presence of catalytic 4-dimethylaminopyridine according to the procedure for the preparation of (3R)-3-ethyl-7-fluoro-4-(4-methoxybenzoyl)-3,4-dihydroquinoxalin-2(1H)-one (see Example 1) to quantitatively yield (3R)-4-(2,4-dimethoxybenzoyl)-3-ethyl-6-fluoro-3,4-dihydroquinoxalin-2(1H)-one. MS (ESI) m/z 359 ([M+H]$^+$); MS (ESI) m/z 357 ([M−H]$^−$).

To a stirred solution of (3R)-4-(2,4-dimethoxybenzoyl)-3-ethyl-6-fluoro-3,4-dihydroquinoxalin-2(1H)-one (0.25 g, 0.73 mmol) in acetonitrile (6 mL) under nitrogen was added cesium carbonate (0.24 g, 0.74 mmol) and iodoethane (0.19 mL, 0.37 g, 2.4 mmol). The mixture was stirred at 89° C. in a sealed tube for 12 h. The solvent was evaporated, and the residue was partitioned between water and methylene chloride. The layers were separated, and the organic layer was washed twice with water, dried over magnesium sulfate, concentrated in vacuo, and purified via Biotage Horizon® (SiO$_2$, gradient from 7% EtOAc/hexane to 51% EtOAc/hexane) to yield 0.20 g (71%) of (3R)-4-(2,4-dimethoxybenzoyl)-1,3-diethyl-6-fluoro-3,4-dihydroquinoxalin-2(1H)-one.

(3R)-4-(2,4-dimethoxybenzoyl)-1,3-diethyl-6-fluoro-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-4-(2,4-dihydroxybenzoyl)-1,3-diethyl-6-fluoro-3,4-dihydroquinoxalin-2(1H)-one (31%). MS (ESI) m/z 359 ([M+H]$^+$); MS (ESI) m/z 357 ([M−H]$^−$); HRMS: calcd for C$_{19}$H$_{19}$FN$_2$O$_4$, 358.1329; found (ESI_FT), 359.13972.

Example 19

(3R)-4-(2,4-Dihydroxybenzoyl)-3-ethyl-6-fluoro-1-methyl-3,4-dihydroquinoxalin-2(1H)-one (3R)-4-(2,4-Dimethoxybenzoyl)-3-ethyl-6-fluoro-3,4-dihydroquinoxalin-2(1H)-one (see Example 18) was treated according to the procedure for the preparation of (3R)-3-ethyl-7-fluoro-4-(4-methoxybenzoyl)-1-methyl-3,4-dihydroquinoxalin-2(1H)-one (see Example 1) to yield (3R)-4-(2,4-dimethoxybenzoyl)-3-ethyl-6-fluoro-1-methyl-3,4-dihydroquinoxalin-2(1H)-one (78%).

(3R)-4-(2,4-Dimethoxybenzoyl)-3-ethyl-6-fluoro-1-methyl-3,4-dihydroquinoxalin-2(1H)-one was treated according to the procedure for the preparation of (3R)-3-ethyl-7-fluoro-4-(4-hydroxybenzoyl)-1-methyl-3,4-dihydroquinoxalin-2(1H)-one (see Example 1) to yield (3R)-4-(2,4-dihydroxybenzoyl)-3-ethyl-6-fluoro-1-methyl-3,4-dihydroquinoxalin-2(1H)-one (49%). MS (ESI) m/z 345 ([M+H]$^+$); MS (ESI) m/z 343 ([M−H]$^−$); HRMS: calcd for C$_{18}$R$_{17}$FN$_2$O$_4$, 344.1172; found (ESI_FT), 345.12407.

Example 20

(3S)-3-Ethyl-6-fluoro-4-[(4-hydroxyphenyl)sulfonyl]-1-propyl-3,4-dihydroquinoxalin-2(1H)-one A solution of 2,4-difluoronitrobenzene (7.75 g, 48.7 mmol) and (S)-2-aminobutyric acid (5.5 g, 53.3 mmol) and potassium carbonate (2.77 g, 20.0 mmol) in dimethylformamide (40 mL), under nitrogen, was stirred at 110° C. for 14 h. The solvent was evaporated at reduced pressure, and the residue was dissolved in 11% potassium carbonate (13.9 g in 125 mL) and washed twice with ether. Concentrated hydrochloric acid (approximately 20 mL) was added dropwise with stirring. The mixture was extracted with ethyl acetate (3×100 mL), and the extracts washed with water (3×100 mL). The solution was dried over magnesium sulfate and the solvent evaporated. The resulting residue crystallized upon standing to yield 7.5 g (63%) of (2S)-2-[(5-fluoro-2-nitrophenyl)amino)]-butanoic acid as a dark orange oil. MS (ESI) m/z [M−H]−=(241).

A solution of (2S)-2-[(5-fluoro-2-nitrophenyl)amino)]-butanoic acid (7.5 g, 31.0 mmol) in ethanol (200 mL) was treated in a Parr apparatus with 10% palladium on carbon (1.50 g) and 50 psi hydrogen gas for 1.5 h, after which time hydrogen uptake had ceased. The mixture was then filtered through Celite, and the solvent was evaporated at reduced pressure. The product was purified via Biotage Horizon® (40M, silica, gradient from 15% EtOAc/hexane to 50% EtOAc/hexane) to yield 6.0 g (quantitative) of (3S)-3-ethyl-6-fluoro-3,4-dihydroquinoxalin-2(1H)-one as a white solid. $[\alpha]_D^{25}$=+18.61° (c=0.010 G/ML, DMSO); MS (ESI) m/z 195 ([M+H]$^+$); Anal. Calcd for C$_{10}$H$_{11}$FN$_2$O: C, 61.85; H, 5.71; N, 14.42. Found: C, 61.72; H, 5.80; N, 14.33.

A solution of (3S)-3-ethyl-6-fluoro-3,4-dihydroquinoxalin-2(H)-one (2.2 g, 11.2 mmol) in methylene chloride (30 mL) was degassed by bubbling nitrogen through the solution for 5 minutes. Ethyl (4-chlorosulfonyl) phenyl carbonate (3.0 g, 11.3 mmol) followed by pyridine (0.92 mL, 11.4 mmol) was added. The reaction was stirred at 25° C. for 14 h, after which time the solvent was removed in vacuo. The resulting residue was dissolved in ethyl acetate and filtered through a plug of silica gel (eluting with 60% EtOAc: hexane). The solution was concentrated in vacuo, and the resulting solid was recrystallized from ethyl acetate:hexane and dried in a vacuum oven to yield 3.6 g (77%) of ethyl 4-{[(2S)-2-ethyl-7-fluoro-3-oxo-3,4-dihydroquinoxalin-1(2H)-yl]sulfonyl}phenyl carbonate. MS (ES) m/z 423.1 ([M+H]$^+$); MS (ES) m/z 440.1 ([M+NH4]$^+$); MS (ES) m/z 445.1 ([M+NA]$^+$); MS (ES) m/z 486.1 ([M+ACN+NA]$^+$); MS (ES) m/z 862.2 ([2M+NH4]$^+$); MS (ES) m/z 867.1 ([2M+NA]$^+$); Anal. Calcd for C$_{19}$H$_{19}$FN$_2$O$_6$S: C, 54.02; H, 4.53; N, 6.63. Found: C, 54.06; H, 4.68; N, 6.45.

To a solution of ethyl 4-{[(2S)-2-ethyl-7-fluoro-3-oxo-3,4-dihydroquinoxalin-1(2H)-yl]sulfonyl}phenyl carbonate (0.35 g, 0.83 mmol) in acetone (5 mL) was added cesium carbonate (0.3 g, 0.91 mmol), and 1-iodopropane (0.32 ml, 3.32 mmol). The mixture was heated at 62° C. for 2.5 hours, cooled to 25° C., and treated with a 2N aqueous solution of sodium hydroxide (3 mL). The reaction was then stirred at 25° C. for 2 hours, and was acidified to pH<2 with the addition of a 2N aqueous solution of hydrochloric acid. The resulting mixture was partitioned between ethyl acetate and a saturated aqueous solution of sodium chloride. The organic layer was separated, dried over magnesium sulfate, and concentrated. The product was purified via flash column chromatography (SiO$_2$, 30% ethyl acetate:hexane eluted to 60% ethyl acetate:hexane) to afford 0.1 g (3S)-3-ethyl-6-fluoro-4-[(4-hydroxyphenyl)sulfonyl]-1-propyl-3,4-dihydroquinoxalin-2(1H)-one as a white solid. MS (ESI) m/z 393 ([M+H]$^+$); MS (ESI) m/z 391 ([M−H]$^−$); Anal. Calcd for C$_{19}$H$_{21}$FN$_2$O$_4$S: C, 58.15; H, 5.39; N, 7.14. Found: C, 57.95; H, 5.46; N, 6.66.

Example 21

(3S)-1-Ethyl-6-fluoro-4-[(4-hydroxyphenyl)sulfonyl]-3-methyl-3,4-dihydroquinoxalin-2(1H)-one 2,4-Difluoronitrobenzene was treated with L-alanine according to the procedure for the preparation of (R)-2-(4-fluoro-2-nitrophenylamino)-butyric acid (see Example 1) to yield N-(5-fluoro-2-nitrophenyl)-L-alanine. MS (ESI) m/z 229 ([M+H]$^+$); MS (ESI) m/z 227 ([M−H]$^−$); Anal. Calcd for C$_9$H$_9$FN$_2$O$_4$: C, 47.37; H, 3.98; N, 12.28. Found: C, 47.61; H, 4.23; N, 12.39.

N-(5-Fluoro-2-nitrophenyl)-L-alanine was treated according to the procedure for the preparation of (3R)-3- ethyl-7-fluoro-3,4-dihydroquinoxalin-2(1H)-one (see Example 1) to yield (3S)-6-fluoro-3-methyl-3,4-dihydroquinoxalin-2(1H)-one. MS (ESI) m/z 181 ([M+H]$^+$); Anal. Calcd for $C_9H_9FN_2O$: C, 59.99; H, 5.03; N, 15.55. Found: C, 59.89; H, 4.88; N, 15.46.

(3S)-6-Fluoro-3-methyl-3,4-dihydroquinoxalin-2(1H)-one was treated according to the procedure for the preparation of 4-{[(2S)-2-ethyl-7-fluoro-3-oxo-3,4-dihydroquinoxalin-1(2H)-yl]sulfonyl}phenyl carbonate (see Example 20) to yield ethyl 4-{[(2S)-7-fluoro-2-methyl-3-oxo-3,4-dihydroquinoxalin-1(2H)-yl]sulfonyl}phenyl carbonate. MS (ESI) m/z 409 ([M+H]$^+$); MS (ESI) m/z 407 ([M–H]$^-$);

Ethyl 4-{[(2S)-7-fluoro-2-methyl-3-oxo-3,4-dihydroquinoxalin-1(2H)-yl]sulfonyl}phenyl carbonate was treated with iodoethane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-1-ethyl-6-fluoro-4-[(4-hydroxyphenyl)sulfonyl]-3-methyl-3,4-dihydroquinoxalin-2(1H)-one. $[\alpha]_D^{25}$=–67° (c=0.005 G/ML, DMSO); MS (ESI) m/z 365 ([M+H]$^+$); MS (ESI) m/z 363 ([M–H]$^-$); Anal. Calcd for $C_{17}H_{17}FN_2O_4S$: C, 56.03; H, 4.70; N, 7.69. Found: C, 54.80; H, 4.47; N, 7.39.

Example 22

(3S)-1-Allyl-3-ethyl-6-fluoro-4-[(4-hydroxyphenyl)sulfonyl]-3,4-dihydroquinoxalin-2(1H)-one 4-{[(2S)-2-ethyl-7-fluoro-3-oxo-3,4-dihydroquinoxalin-1(2H)-yl]sulfonyl}phenyl carbonate (see Example 20) was treated with allyl bromide according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-1-allyl-3-ethyl-6-fluoro-4-[(4-hydroxyphenyl)sulfonyl]-3,4-dihydroquinoxalin-2(1H)-one. $[\alpha]_D^{25}$=–20° (c=0.005 G/ML, DMSO); MS (ESI) m/z 391 ([M+H]$^+$); MS (ESI) m/z 389 ([M–H]$^-$); Anal. Calcd for $C_{19}H_{19}FN_2O_4S$: C, 58.45; H, 4.91; N, 7.17. Found: C, 54.53; H, 4.50; N, 6.22.

Example 23

(3S)-1-Butyl-3-ethyl-6-fluoro-4-[(4-hydroxyphenyl)sulfonyl]-3,4-dihydroquinoxalin-2(1H)-one 4-{[(2S)-2-ethyl-7-fluoro-3-oxo-3,4-dihydroquinoxalin-1(2H)-yl]sulfonyl}phenyl carbonate (see Example 20) was treated with 1-bromobutane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-1-Butyl-3-ethyl-6-fluoro-4-[(4-hydroxyphenyl)sulfonyl]-3,4-dihydroquinoxalin-2(1H)-one. $[\alpha]_D^{25}$=–4° (c=0.0058 G/ML, DMSO); MS (ESI) m/z 407 ([M+H]$^+$); MS (ESI) m/z 405 ([M–H]$^-$);

Example 24

(3S)-1-benzyl-3-ethyl-6-fluoro-4-[(4-hydroxyphenyl)sulfonyl]-3,4-dihydroquinoxalin-2(1H)-one 4-{[(2S)-2-ethyl-7-fluoro-3-oxo-3,4-dihydroquinoxalin-1(2H)-yl]sulfonyl}phenyl carbonate (see Example 20) was treated with benzyl bromide according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-1-benzyl-3-ethyl-6-fluoro-4-[(4-hydroxyphenyl)sulfonyl]-3,4-dihydroquinoxalin-2(1H)-one. $[\alpha]_D^{25}$=–30° (c=0.0058 G/ML, DMSO); MS (ESI) m/z 441 ([M+H]$^+$); MS (ESI) m/z 439 ([M–H]$^-$); Anal. Calcd for $C_{23}H_{21}FN_2O_4S$: C, 62.71; H, 4.81; N, 6.36. Found: C, 62.23; H, 4.49; N, 6.23.

Example 25

(3S)-3-Ethyl-6-fluoro-4-[(4-hydroxyphenyl)sulfonyl]-1-methyl-3,4-dihydroquinoxalin-2(1H)-one 4-{[(2S)-2-ethyl-7-fluoro-3-oxo-3,4-dihydroquinoxalin-1(2H)-yl]sulfonyl}phenyl carbonate (see Example 20) was treated with iodomethane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-3-ethyl-6-fluoro-4-[(4-hydroxyphenyl)sulfonyl]-1-methyl-3,4-dihydroquinoxalin-2(1H)-one. $[\alpha]_D^{25}$=–14° (c=0.0041 G/ML, DMSO); MS (ESI) m/z 365 ([M+H]$^+$); MS (ESI) m/z 363 ([M–H]$^-$); HRMS: calcd for $C_{17}H_{17}FN_2O_4S$, 364.0893; found (ESI+), 365.09603.

Example 26

(3S)-1,3-Diethyl-6-fluoro-4-[(4-hydroxyphenyl)sulfonyl]-3,4-dihydroquinoxalin-2(1H)-one 4-{[(2S)-2-ethyl-7-fluoro-3-oxo-3,4-dihydroquinoxalin-1(2H)-yl]sulfonyl}phenyl carbonate (see Example 20) was treated with iodoethane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-1,3-diethyl-6-fluoro-4-[(4-hydroxyphenyl)sulfonyl]-3,4-dihydroquinoxalin-2(1H)-one. $[\alpha]_D^{25}$=–7° (c=0.0077 G/ML, DMSO); MS (ESI) m/z 379 ([M+H]$^+$); MS (ESI) m/z 377 ([M–H]$^-$); HRMS: calcd for $C_{18}H_{19}FN_2O_4S$, 378.1050; found (ESI+), 379.11178.

Example 27

(3S)-1,3-diethyl-4-[(4-hydroxyphenyl)sulfonyl]-6-methyl-3,4-dihydroquinoxalin-2(1H)-one 3-Fluoro-4-nitrotoluene was treated with (S)-2-aminobutyric acid according to the procedure for the preparation of (R)-2-(4-fluoro-2-nitrophenylamino)-butyric acid (see Example 1) to yield (S)-2-(5-methyl)-2-(nitrophenylamino)-butyric acid.

(S)-2-(5-Methyl)-2-(nitrophenylamino)-butyric acid was treated according to the procedure for the preparation of (3R)-3-ethyl-7-fluoro-3,4-dihydroquinoxalin-2(1H)-one (see Example 1) to yield (3S)-3-ethyl-6-methyl-3,4-dihydroquinoxalin-2(1H)-one. $[\alpha]_D^{25}$=+57.6° (c=0.0057 G/ML, DMSO); MS (ESI) m/z 191 ([M+H]$^+$).

(3S)-3-Ethyl-6-methyl-3,4-dihydroquinoxalin-2(1H)-one was treated according to the procedure for the preparation of 4-{[(2S)-2-ethyl-7-fluoro-3-oxo-3,4-dihydroquinoxalin-1(2H)-yl]sulfonyl}phenyl carbonate (see Example 20) to yield ethyl 4-{[(2S)-2-ethyl-7-methyl-3-oxo-3,4-dihydroquinoxalin-1(2H)-yl]sulfonyl}phenyl carbonate. $[\alpha]_D^{25}$=+3.5° (c=0.0063 G/ML, DMSO); MS (ESI) m/z 419 ([M+H]$^+$); MS (ESI) m/z 417 ([M–H]$^-$).

Ethyl 4-{[(2S)-2-ethyl-7-methyl-3-oxo-3,4-dihydroquinoxalin-1(2H)-yl]sulfonyl}phenyl carbonate was treated with iodoethane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-1,3-diethyl-4-[(4-hydroxyphenyl)sulfonyl]-6-methyl-3,4-dihydroquinoxalin-2(1H)-one $[\alpha]_D^{25}$=−118° (c=0.0054 G/ML, DMSO); MS (ESI) m/z 375 ([M+H]$^+$); MS (ESI) m/z 373 ([M−H]$^−$); Anal. Calcd for $C_{19}H_{22}N_2O_4S$: C, 60.94; H, 5.92; N, 7.48. Found: C, 61.50; H, 5.99; N, 6.89.

Example 28

(3S)-3-Ethyl-4-[(4-hydroxyphenyl)sulfonyl]-1,6-dimethyl-3,4-dihydroquinoxalin-2(1H)-one 4-{[(2S)-2-ethyl-7-fluoro-3-oxo-3,4-dihydroquinoxalin-1(2H)-yl]sulfonyl}phenyl carbonate (see Example 20) was treated with iodomethane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-3-ethyl-4-[(4-hydroxyphenyl)sulfonyl]-1,6-dimethyl-3,4-dihydroquinoxalin-2(1H)-one. $[\alpha]_D^{25}$=−123° (c=0.0057 G/ML, DMSO); MS (ESI) m/z 361 ([M+H]$^+$); MS (ESI) m/z 359 ([M−H]$^−$); Anal. Calcd for $C_{18}H_{20}N_2O_4S$: C, 59.98; H, 5.59; N, 7.77. Found: C, 57.75; H, 5.20; N, 7.42.

Example 29

(3S)-3-Ethyl-7-fluoro-4-[(4-hydroxyphenyl)sulfonyl]-1-methyl-3,4-dihydroquinoxalin-2(1H)-one 2,5-Difluoronitrobenzene was treated with (S)-2-aminobutyric acid according to the procedure for the preparation of (R)-2-(4-fluoro-2-nitrophenylamino)-butyric acid (see Example 1) to yield (2S)-2-[(4-fluoro-2-nitrophenyl)amino]butanoic acid. MS (ESI) m/z 243 ([M+H]$^+$); MS (ESI) m/z 241 ([M−H]$^−$).

(2S)-2-[(4-Fluoro-2-nitrophenyl)amino]butanoic acid was treated according to the procedure for the preparation of (3R)-3-ethyl-7-fluoro-3,4-dihydroquinoxalin-2(1H)-one (see Example 1) to yield (3S)-3-ethyl-7-fluoro-3,4-dihydroquinoxalin-2(1H)-one. $[\alpha]_D^{25}$=+33.42° (c=0.01 G/ML, DMSO); MS (ESI) m/z 195 ([M+H]$^+$); Anal. Calcd for $C_{10}H_{11}FN_2O$: C, 61.85; H, 5.71; N, 14.42. Found: C, 61.84; H, 5.72; N, 14.24.

(3S)-3-Ethyl-7-fluoro-3,4-dihydroquinoxalin-2(1H)-one was treated with 4-methoxybenzenesulfonyl chloride according to the procedure for the preparation of ethyl 4-{[(2S)-2-ethyl-7-fluoro-3-oxo-3,4-dihydroquinoxalin-1(2H)-yl]sulfonyl}phenyl carbonate (see Example 20) to yield (3S)-3-ethyl-7-fluoro-4-[(4-methoxyphenyl)sulfonyl]-3,4-dihydroquinoxalin-2(1H)-one. $[\alpha]_D^{25}$=−12.1° (c=0.006 G/ML, DMSO); MS (ESI) m/z 365 ([M+H]$^+$); MS (ESI) m/z 363 ([M−H]$^−$); Anal. Calcd for $C_{17}H_{17}FN_2O_4S$: C, 56.03; H, 4.70; N, 7.69. Found: C, 55.99; H, 4.57; N, 7.62.

(3S)-3-Ethyl-7-fluoro-4-[(4-methoxyphenyl)sulfonyl]-3,4-dihydroquinoxalin-2(1H)-one was treated with iodomethane according to the procedure for the preparation of (3R)-3-ethyl-7-fluoro-4-(4-methoxybenzoyl)-1-methyl-3,4-dihydroquinoxalin-2(1H)-one (see Example 1) to yield (3S)-3-ethyl-7-fluoro-4-[(4-methoxyphenyl)sulfonyl]-1-methyl-3,4-dihydroquinoxalin-2(1H)-one. MS (ESI) m/z 379 ([M+H]$^+$).

A solution of (3S)-3-ethyl-7-fluoro-4-[(4-methoxyphenyl)sulfonyl]-1-methyl-3,4-dihydroquinoxalin-2(1H)-one (0.27 g, 0.7 mmol) and tetrabutylamonium iodide (0.77 g, 2.09 mmol) in methylene chloride (20 mL) was cooled to −78° C. and treated with a 1M solution of boron trichloride in methylene chloride (3.5 mL, 3.5 mmol) via syringe. The cooling bath was removed and the solution was stirred at 25° C. for 3 hours. The reaction was quenched with a saturated aqueous solution of ammonium chloride. The organic phase was separated, dried over magnesium sulfate and concentrated in vacuo. The crude oil was purified via flash column chromatography (SiO$_2$, 40% ethyl acetate:hexane) to afford 0.2 g (78%) of (3S)-3-ethyl-7-fluoro-4-[(4-hydroxyphenyl)sulfonyl]-1-methyl-3,4-dihydroquinoxalin-2(1H)-one as white solid. MS (ESI) m/z 365 ([M+H]$^+$); MS (ESI) m/z 363 ([M−H]$^−$); Anal. Calcd for $C_{17}H_{17}FN_2O_4S$: C, 56.03; H, 4.70; N, 7.69. Found: C, 56.12; H, 4.03; N, 7.45.

Example 30

(3S)-1,3-Diethyl-7-fluoro-4-[(4-hydroxyphenyl)sulfonyl]-3,4-dihydroquinoxalin-2(1H)-one (3S)-3-Ethyl-7-fluoro-4-[(4-methoxyphenyl)sulfonyl]-3,4-dihydroquinoxalin-2(1H)-one (see Example 29) was treated with iodoethane according to the procedure for the preparation of (3R)-3-ethyl-7-fluoro-4-(4-methoxybenzoyl)-1-methyl-3,4-dihydroquinoxalin-2(1H)-one (see Example 1) to yield (3S)-1,3-diethyl-7-fluoro-4-[(4-methoxyphenyl)sulfonyl]-3,4-dihydroquinoxalin-2(1H)-one. MS (ESI) m/z 393 ([M+H]$^+$); Anal. Calcd for $C_{19}H_{21}FN_2O_4S$: C, 58.15; H, 5.39; N, 7.14. Found: C, 58.36; H, 5.56; N, 7.05.

(3S)-1,3-Diethyl-7-fluoro-4-[(4-methoxyphenyl)sulfonyl]-3,4-dihydroquinoxalin-2(1H)-one was treated according to the procedure for the preparation of (3S)-3-ethyl-7-fluoro-4-[(4-hydroxyphenyl)sulfonyl]-1-methyl-3,4-dihydroquinoxalin-2(1H)-one (see Example 29) to yield (3S)-1,3-Diethyl-7-fluoro-4-[(4-hydroxyphenyl)sulfonyl]-3,4-dihydroquinoxalin-2(1 h)-one. MS (ESI) m/z 379 ([M+H]$^+$); MS (ESI) m/z 377 ([M−H]$^−$).

Example 31

(3S)-7-Bromo-1,3-diethyl-4-[(4-hydroxyphenyl)sulfonyl]-3,4-dihydroquinoxalin-2(1H)-one 5-Bromo-2-fluoronitrobenzene was treated with (S)-2-aminobutyric acid according to the procedure for the preparation of (R)-2-(4-fluoro-2-nitrophenylamino)-butyric acid (see Example 1) to yield (2S)-2-[(4-bromo-2-nitrophenyl)amino]butanoic acid. MS (ESI) m/z 303/305 ([M+H]$^+$); MS (ESI) m/z 301/303 ([M−H]$^−$).

A solution of (2S)-2-[(4-Bromo-2-nitrophenyl)amino]butanoic acid (8.3 g, 27.4 mmol) in methanol (20 mL) and acetic acid (20 mL) was treated with iron filings (5.0 g, 89.5 mmol). The reaction was heated at reflux for 3 h, after which time the reaction was cooled, and filtered. The filtrate was concentrated in vacuo, and the resulting residue was diluted with ethyl acetate, washed with a saturated aqueous solution of sodium bicarbonate, dried over magnesium sulfate, and concentrated in vacuo to yield 3.8 g (54%) of (3S)-7-bromo-3-ethyl-3,4-dihydroquinoxalin-2(1H)-one as a yellow solid. $[\alpha]_D^{25}$=+33.23° (c=0.008 G/ML, DMSO); MS (ESI) m/z 255/257 ([M+H]$^+$); Anal. Calcd for $C_{10}H_{11}BrN_2O$: C, 47.08; H, 4.35; N, 10.98. Found: C, 46.98; H, 4.08; N, 10.90.

(3S)-7-Bromo-3-ethyl-3,4-dihydroquinoxalin-2(1H)-one was treated according to the procedure for the preparation of 4-{[(2S)-2-ethyl-7-fluoro-3-oxo-3,4-dihydroquinoxalin-1(2H)-yl]sulfonyl}phenyl carbonate (see Example 20) to yield 4-{[(2S)-6-bromo-2-ethyl-3-oxo-3,4-dihydroquinoxalin-1(2H)-yl]sulfonyl}phenyl ethyl carbonate. $[\alpha]_D^{25}$=−81.2° (c=0.0054 G/ML, DMSO); MS (ESI) m/z 483/485

([M+H]$^+$); MS (ESI) m/z 481/483 ([M−H]$^−$); Anal. Calcd for $C_{19}H_{19}BrN_2O_6S$: C, 47.22; H, 3.96; N, 5.80. Found: C, 47.32; H, 3.96; N, 5.71.

4-{[(2S)-6-Bromo-2-ethyl-3-oxo-3,4-dihydroquinoxalin-1 (2H)-yl]sulfonyl}phenyl ethyl carbonate was treated with iodoethane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-7-bromo-1,3-diethyl-4-[(4-hydroxyphenyl)sulfonyl]-3,4-dihydroquinoxalin-2(1H)-one. $[\alpha]_D^{25}$=−780 (c=0.005 G/ML, DMSO); MS (ESI) m/z 439/441 ([M+H]$^+$); MS (ESI) m/z 437/439 ([M−H]$^−$).

Example 32

(3S)-7-bromo-3-ethyl-4-[(4-hydroxyphenyl)sulfonyl]-1-methyl-3,4-dihydroquinoxalin-2(1H)-one 4-{[(2S)-6-Bromo-2-ethyl-3-oxo-3,4-dihydroquinoxalin-1 (2H)-yl]sulfonyl}phenyl ethyl carbonate was treated with iodomethane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-7-bromo-3-ethyl-4-[(4-hydroxyphenyl)sulfonyl]-1-methyl-3,4-dihydroquinoxalin-2(1H)-one. $[\alpha]_D^{25}$=−121° (c=0.0052 G/ML, DMSO); MS (ESI) m/z 425/427 ([M+H]$^+$); MS (ESI) m/z 423/425 ([M−H]$^−$); Anal. Calcd for $C_{17}H_{17}BrN_2O_4S$: C, 48.01; H, 4.03; N, 6.59. Found: C, 47.74; H, 4.17; N, 6.22.

Example 33

(3S)-6-bromo-1,3-diethyl-4-[(4-hydroxyphenyl)sulfonyl]-3,4-dihydroquinoxalin-2(1H)-one 4-Bromo-2-fluoronitrobenzene was treated with (S)-2-aminobutyric acid according to the procedure for the preparation of (R)-2-(4-fluoro-2-nitrophenylamino)-butyric acid (see Example 1) to yield (2S)-2-[(5-bromo-2-nitrophenyl)amino]butanoic acid.

(2S)-2-[(5-bromo-2-nitrophenyl)amino]butanoic acid was treated according to the procedure for the preparation of (3S)-7-bromo-3-ethyl-3,4-dihydroquinoxalin-2(1H)-one (see Example 31) to yield (3S)-6-bromo-3-ethyl-3,4-dihydroquinoxalin-2(1H)-one.

(3S)-6-bromo-3-ethyl-3,4-dihydroquinoxalin-2(1H)-one was treated according to the procedure for the preparation of 4-{[(2S)-2-ethyl-7-fluoro-3-oxo-3,4-dihydroquinoxalin-1 (2H)-yl]sulfonyl}phenyl carbonate (see Example 20) to yield 4-{[(2S)-7-bromo-2-ethyl-3-oxo-3,4-dihydroquinoxalin-1 (2H)-yl]sulfonyl}phenyl ethyl carbonate.

4-{[(2S)-7-Bromo-2-ethyl-3-oxo-3,4-dihydroquinoxalin-1(2H)-yl]sulfonyl}phenyl ethyl carbonate was treated with iodoethane according to the procedure for the preparation of (3S)-3-ethyl-6-fluoro-4-[(4-hydroxyphenyl)sulfonyl]-1-propyl-3,4-dihydroquinoxalin-2(1H)-one (see Example 20) to yield (3S)-6-bromo-1,3-diethyl-4-[(4-hydroxyphenyl)sulfonyl]-3,4-dihydroquinoxalin-2(1H)-one. $[\alpha]_D^{25}$=−190° (c=0.0052 G/ML, DMSO); MS (ESI) m/z 439/441 ([M+H]$^+$); MS (ESI) m/z 437/439 ([M−H]$^−$); Anal. Calcd for $C_{18}H_{19}BrN_2O_4S$: C, 49.21; H, 4.36; N, 6.38. Found: C, 50.41; H, 5.02; N, 6.00.

Example 34

(3S)-6-bromo-3-ethyl-4-[(4-hydroxyphenyl)sulfonyl]-1-methyl-3,4-dihydroquinoxalin-2(1H)-one 4-{[(2S)-7-Bromo-2-ethyl-3-oxo-3,4-dihydroquinoxalin-1 (2H)-yl]sulfonyl}phenyl ethyl carbonate (see Example 33) was treated with iodomethane according to the procedure for the preparation of (3S)-3-ethyl-6-fluoro-4-[(4-hydroxyphenyl)sulfonyl]-1-propyl-3,4-dihydroquinoxalin-2 (1H)-one (see Example 20) to yield (3S)-6-bromo-3-ethyl-4-[(4-hydroxyphenyl)sulfonyl]-1-methyl-3,4-dihydroquinoxalin-2(1H)-one. MS (ESI) m/z 425/427 ([M+H]$^+$); MS (ESI) m/z 423/425 ([M−H]$^−$); Anal. Calcd for $C_{17}H_{17}BrN_2O_4S$: C, 48.01; H, 4.03; N, 6.59. Found: C, 48.07; H, 4.27; N, 6.37.

Example 35

IL-6 and Creatine Kinase Assays

ERα infected HAECT-1 cells or control cells were thawed, diluted 42× in warm EBM-BSA, plated into 96-well plates at 0.1 ml/well and incubated for 4 h at 34° C. Test compounds were added to the cells as 2× stocks in EBM-BSA containing 2 ng/ml IL-1β (R&D Systems) and plates were returned to the incubator (34° C.). After 15-20 h, 100 μl aliquots of media were removed from the cells and assayed for IL-6 content using a BioSource human IL-6 ELISA Kit. Cells were subsequently washed with 300 μl of Dulbecco's phosphate buffered saline and lysed in 50 μl of Cell Culture Lysis Reagent (Promega). Creatine kinase was determined from the rate of increase in $A_{340}$ following addition of 100 μl of CK assay reagent (Sigma, cat. No 47-10) to the remainder of the cell lysate.

Data Analyses

For $IC_{50}$ and $EC_{50}$ calculations, mean IL-6 or CK values versus $\log_{10}$ of the compound concentration were fitted to a four parameter logistic equation. The $IC_{50}/EC_{50}$ value, 'Hill slope', upper and lower limits of the curve were iteratively estimated.

The following summarizes the results obtained in the standard pharmacological test procedures described above, Table 1 displays results for effects of 17-β-estradiol on IL-6 and CK expression in Ad5-wt-ER infected HAECT-1 cells.

TABLE 1

| Example # | ER/IL-6 $IC_{50}$ (nM) | ER/IL-6 % E2 | ER/CK $EC_{50}$ (nM) | ER/CK % E2 |
|---|---|---|---|---|
| Example 1 | 74 | 99 | 89 | 16 |
| Example 2 | 1228 | 80 | >10 uM | 24 |
| Example 3 | 72 | 104 | 103 | 29 |
| Example 4 | 520 | 57 | 126 | 19 |
| Example 5 | 542 | 65 | 255 | 17 |
| Example 6 | 285 | 44 | | |
| Example 7 | 303 | 44 | | |
| Example 8 | 139 | 99 | | |
| Example 9 | 222 | 96 | | |

TABLE 1-continued

| Example # | ER/IL-6 IC$_{50}$ (nM) | ER/IL-6 % E2 | ER/CK EC$_{50}$ (nM) | ER/CK % E2 |
|---|---|---|---|---|
| Example 10 | 57 | 95 | | |
| Example 11 | 105 | 91 | | |
| Example 12 | 52 | 95 | | |
| Example 13 | 89 | 102 | | |
| Example 14 | 262 | 87 | | |
| Example 15 | 102 | 84 | | |
| Example 16 | 204 | 83 | | |
| Example 17 | 445 | 96 | | |
| Example 18 | 20 | 96 | 169 | 36 |
| Example 19 | 5.4 | 92 | 50 | 44 |
| Example 20 | 157 | 79 | | |
| Example 21 | 181 | 56 | | |
| Example 22 | 5604 | 55 | | |
| Example 23 | 313 | 106 | | |
| Example 24 | 534 | 40 | | |
| Example 25 | 681 | 108 | >3 uM | 35 |
| Example 26 | 339 | 81 | inactive | |
| Example 27 | 447 | 63 | | |
| Example 28 | 296 | 92 | | |
| Example 29 | 1169 | 85 | 344 | 20 |
| Example 30 | 738 | 63 | 43 | 9 |
| Example 31 | 1573 | 71 | | |
| Example 32 | 429 | 90 | | |
| Example 33 | 413 | 92 | | |
| Example 34 | 258 | 128 | | |

Efficacy values are relative to the maximal inhibition (IL-6 test procedure) or stimulation (CK test procedure) observed with E2.

E2 inhibits NF-κB and IL-6 expression in Ad5-wt-ER infected HAECT-1 cells with an IC$_{50}$ value around 1 nM and induces expression of creatine kinase in the same cells with similar potency (5.8 nM) (Table 1). In contrast, compounds of the present invention potently and efficaciously inhibit IL-6 expression in Ad5-wt-ER infected HAECT-1 cells but do not induce CK expression (Table 1) in an ER-dependent manner. The ability of compounds of the present invention to inhibit IL-6 expression without inducing CK activity (Table 1) demonstrates anti-inflammatory activity in the absence of classic estrogenic activity.

The disclosures of each patent, patent application, and publication cited or described in this document are hereby incorporated herein by reference, in their entireties.

Various modifications of the invention, in addition to those described herein, will be apparent to those skilled in the art from the foregoing description. Such modifications are also intended to fall within the scope of the appended claims.

What is claimed:

1. A compound of the structure I:

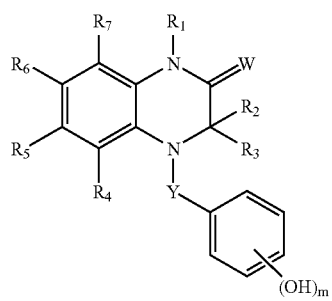

I or a pharmaceutically acceptable salt thereof;

wherein:

m is 1, 2, 3, 4, or 5;

n is, independently, 0, 1, 2, 3, 4, or 5;

W is O or C(R$_8$)$_2$;

Y is (C(R$_8$)$_2$)$_n$—X—(C(R$_8$)$_2$)$_n$, wherein X is a bond, O, OC(=O), C(=O), or S(O)$_2$;

R$_1$ is H, C$_1$-C$_6$ alkyl, C$_2$-C$_7$ alkenyl, cycloalkyl, cycloalkenyl, or arylalkyl;

R$_2$ and R$_3$ are each, independently, H, C$_1$-C$_6$ alkyl, or C$_2$-C$_7$ alkenyl, provided that both are not H;

R$_4$, R$_5$, R$_6$, and R$_7$ are each, independently, H, C$_1$-C$_6$ alkyl, C$_2$-C$_7$ alkenyl, hydroxyl, alkoxy, aryloxy, halogen, trifluoromethyl, CN, NO$_2$, C(=O)R$_8$, or C(=O)OR$_8$; and R$_8$ is, independently, H, C$_1$-C$_6$ alkyl, or phenyl, wherein each of said C$_1$-C$_6$ alkyl, said C$_2$-C$_7$ alkenyl, said cycloalkyl, said cycloalkenyl, said alkoxy, said arylalkyl, said aryloxy, and said phenyl is optionally substituted with 1-3 moieties independently selected from the group consisting of halogen, C$_1$-C$_6$ alkyl, C$_2$-C$_6$ alkenyl, C$_2$-C$_6$ alkynyl, NR$_4$R$_5$, N[(CH$_2$)$_2$]$_2$O, N[(CH$_2$)$_2$]$_2$NR$_4$, NHSO$_2$R$_4$, NR$_4$C(=O)R$_5$, NHC(=O)OR$_4$, NO$_2$, SO$_2$NR$_4$R$_5$, SO$_2$R$_4$, OR$_4$, C(=O)R$_4$, COOR$_4$, CONR$_4$R$_5$, and CN.

2. The compound of claim 1, or a pharmaceutically acceptable salt thereof, wherein m is 1 or 2.

3. The compound of claim 1, or pharmaceutically acceptable salt thereof, wherein R$_1$ is substituted with at least one halogen.

4. The compound of claim 1, or a pharmaceutically acceptable salt thereof, wherein n is 0 at each occurrence and X is C(=O).

5. The compound of claim 4, or a pharmaceutically acceptable salt thereof, wherein R$_1$ is C$_1$-C$_6$ alkyl, C$_2$-C$_7$ alkenyl, cycloalkyl, or cycloalkenyl, wherein each of said C$_1$-C$_6$ alkyl, said C$_2$-C$_7$ alkenyl, said cycloalkyl and said cycloalkenyl is optionally substituted.

6. The compound of claim 4, or a pharmaceutically acceptable salt thereof, wherein R$_1$ is C$_1$-C$_6$ alkyl, C$_2$-C$_7$ alkenyl, or cycloalkyl, wherein each of said $C_1$-$C_6$ alkyl, said $C_2$-$C_7$ alkenyl, and said cycloalkyl is optionally substituted.

7. The compound of claim 1, or a pharmaceutically acceptable salt thereof, wherein n is 0 at each occurrence and X is $S(O)_2$.

8. The compound of claim 7, or a pharmaceutically accepetable salt thereof, wherein $R_1$ is $C_1$-$C_6$ alkyl, $C_2$-$C_7$ alkenyl, or arylalkyl, wherein each of said $C_1$-$C_6$ alkyl, said $C_2$-$C_7$ alkenyl, and said arylalkyl is optionally substituted.

9. The compound of claim 1, or a pharmaceutically accepetable salt thereof, wherein $R_1$ is $C_1$-$C_6$ alkyl, $C_2$-$C_7$ alkenyl, wherein each of said $C_1$-$C_6$ alkyl and said $C_2$-$C_7$ alkenyl is optionally substituted.

10. The compound of claim 1, or a pharmaceutically acceptable salt thereof, wherein $R_2$ is $C_1$-$C_6$ alkyl or $C_2$-$C_7$ alkenyl, and $R_3$ is H, wherein each of said $C_1$-$C_6$ alkyl and said $C_2$-$C_7$ alkenyl is optionally substituted.

11. The compound of claim 1, or a pharmaceutically acceptable salt thereof, wherein $R_2$ is $C_1$-$C_3$ alkyl or $C_2$-$C_4$ alkenyl, and $R_3$ is H, wherein each of said $C_1$-$C_3$ alkyl and said $C_2$-$C_4$ alkenyl is optionally substituted.

12. The compound of claim 1, or a pharmaceutically acceptable salt thereof, wherein $R_4$, $R_5$, $R_6$, and $R_7$ are each, independently, $C_1$-$C_6$ alkyl, $C_2$-$C_7$ alkenyl, hydroxyl, alkoxy, halogen, or trifluoromethyl, wherein each of said $C_1$-$C_6$ alkyl, and $C_2$-$C_7$ alkenyl, and alkoxy is optionally substituted.

13. The compound of claim 1, or a pharmaceutically acceptable salt thereof, wherein $R_4$, $R_5$, $R_6$, and $R_7$ are each, independently, H, $C_1$-$C_3$ alkyl, $C_2$-$C_4$ alkenyl, halogen, or trifluoromethyl, wherein each of said $C_1$-$C_3$ alkyl and said $C_2$-$C_4$ alkenyl is optionally substituted.

14. The compound of claim 1, or a pharmaceutically acceptable salt thereof, wherein the compound is
- (3R)-3-ethyl-7-fluoro-4-(4-hydroxybenzoyl)-1-methyl-3,4-dihydroquinoxalin-2(1H)-one;
- (3R)-1-benzyl-3-ethyl-7-fluoro-4-(4-hydroxybenzoyl)-3,4-dihydroquinoxalin-2(1H)-one;
- (3R)-1,3-diethyl-7-fluoro-4-(4-hydroxybenzoyl)-3,4-dihydroquinoxalin-2(1H)-one;
- (3R)-3-ethyl-7-fluoro-4-(3 hydroxybenzoyl)-1-methyl-3,4-dihydroquinoxalin-2(1H)-one;
- (3R)-1-benzyl-3-ethyl-7-fluoro-4-(3-hydroxybenzoyl)-3,4-dihydroquinoxalin-2(1H)-one;
- (3S)-1,3-diethyl-6-fluoro-4-(4-hydroxybenzoyl)-3,4-dihydroquinoxalin-2(1H)-one;
- (3S)-3-ethyl-6-fluoro-4-(4-hydroxybenzoyl)-1-methyl-3,4-dihydroquinoxalin-2(1H)-one;
- (3R)-1,3-diethyl-6-fluoro-4-(4-hydroxybenzoyl)-3,4-dihydroquinoxalin-2(1H)-one;
- (3R)-3-ethyl-6-fluoro-4-(4-hydroxybenzoyl)-1-propyl-3,4-dihydroquinoxalin-2(1H)-one;
- (3R)-1-allyl-3-ethyl-6-fluoro-4-(4-hydroxybenzoyl)-3,4-dihydroquinoxalin-2(1H)-one;
- (3R)-3-ethyl-6-fluoro-4-(4-hydroxybenzoyl)-1-isopropyl-3,4-dihydroquinoxalin-2(1H)-one;
- (3R)-1-butyl-3-ethyl-6-fluoro-4-(4-hydroxybenzoyl)-3,4-dihydroquinoxalin-2(1H)-one;
- (3R)-3-ethyl-6-fluoro-4-(4-hydroxybenzoyl)-1-pentyl-3,4-dihydroquinoxalin-2(1H)-one;
- (3R)-3-ethyl-6-fluoro-4-(4-hydroxybenzoyl)-1-isobutyl-3,4-dihydroquinoxalin-2(1H)-one;
- (3R)-3-ethyl-6-fluoro-4-(4-hydroxybenzoyl)-1-methyl-3,4-dihydroquinoxalin-2(1H)-one;
- (3R)-3-ethyl-6-fluoro-4-(4-hydroxybenzoyl)-1-(2,2,2-trifluoroethyl)-3,4-dihydroquinoxalin-2(1H)-one;
- (3R)-1-cyclopentyl-3-ethyl-6-fluoro-4-(4-hydroxybenzoyl)-3,4-dihydroquinoxalin-2(1H)-one;
- (3R)-4-(2,4-dihydroxybenzoyl)-1,3-diethyl-6-fluoro-3,4-dihydroquinoxalin-2(1H)-one;
- (3R)-4-(2,4-dihydroxybenzoyl)-3-ethyl-6-fluoro-1-methyl-3,4-dihydroquinoxalin-2(1H)-one;
- (3S)-3-ethyl-6-fluoro-4-[(4-hydroxyphenyl)sulfonyl]-1-propyl-3,4-dihydroquinoxalin-2(1H)-one;
- (3S)-1-ethyl-6-fluoro-4-[(4-hydroxyphenyl)sulfonyl]-3-methyl-3,4-dihydroquinoxalin-2(1H)-one;
- (3S)-1-allyl-3-ethyl-6-fluoro-4-[(4-hydroxyphenyl)sulfonyl]-3,4-dihydroquinoxalin-2(1H)-one;
- (3S)-1-butyl-3-ethyl-6-fluoro-4-[(4-hydroxyphenyl)sulfonyl]-3,4-dihydroquinoxalin-2(1H)-one;
- (3S)-1-benzyl-3-ethyl-6-fluoro-4-[(4-hydroxyphenyl)sulfonyl]-3,4-dihydroquinoxalin-2(1H)-one;
- (3S)-3-ethyl-6-fluoro-4-[(4-hydroxyphenyl)sulfonyl]-1-methyl-3,4-dihydroquinoxalin-2(1H)-one;
- (3S)-1,3-diethyl-6-fluoro-4-[(4-hydroxyphenyl)sulfonyl]-3,4-dihydroquinoxalin-2(1H)-one;
- (3S)-1,3-diethyl-4-[(4-hydroxyphenyl)sulfonyl]-6-methyl-3,4-dihydroquinoxalin-2(1H)-one;
- (3S)-3-ethyl-4-[(4-hydroxyphenyl)sulfonyl]-1,6-dimethyl-3,4-dihydroquinoxalin-2(1H)-one;
- (3S)-3-ethyl-7-fluoro-4-[(4-hydroxyphenyl)sulfonyl]-1-methyl-3,4-dihydroquinoxalin-2(1H)-one;
- (3S)-1,3-diethyl-7-fluoro-4-[(4-hydroxyphenyl)sulfonyl]-3,4-dihydroquinoxalin-2(1H)-one;
- (3S)-7-bromo-1,3-diethyl-4-[(4-hydroxyphenyl)sulfonyl]-3,4-dihydroquinoxalin-2(1H)-one;
- (3S)-7-bromo-3-ethyl-4-[(4-hydroxyphenyl)sulfonyl]-1-methyl-3,4-dihydroquinoxalin-2(1H)-one;
- (3S)-6-bromo-1,3-diethyl-4-[(4-hydroxyphenyl)sulfonyl]-3,4-dihydroquinoxalin-2(1H)-one;

or (3S)-6-bromo-3-ethyl-4-[(4-hydroxyphenyl)sulfonyl]-1-methyl-3,4-dihydroquinoxalin-2(1H)-one.

15. A compound of the structure II:

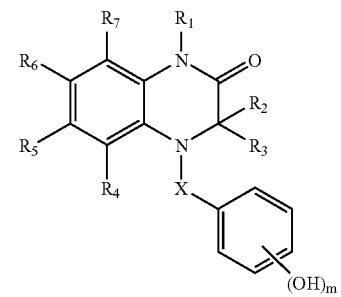

or pharmaceutically acceptable salt thereof
wherein:

m is 1, 2, or 3;

X is C(=O) or $S(O)_2$;

$R_1$ is H, $C_1$-$C_6$ alkyl, $C_2$-$C_7$ alkenyl, cycloalkyl, cycloalkenyl, or arylalkyl;

$R_2$ and $R_3$ are each, independently, H, $C_1$-$C_6$ alkyl, $C_2$-$C_7$ alkenyl, provided that both are not H;

$R_4$, $R_5$, $R_6$, and $R_7$ are each, independently, H, $C_1$-$C_6$ alkyl, $C_2$-$C_7$ alkenyl, hydroxyl, alkoxy, aryloxy, halogen, trifluoromethyl, CN, $NO_2$, C(=O)$R_8$, or C(=O)O$R_8$; and $R_8$ is H, $C_1$-$C_6$ alkyl, or phenyl, wherein each of said $C_1$-$C_6$ alkyl, said $C_2$-$C_7$ alkenyl said cycloalkyl, said cyoloalkenyl, said alkoxy, said arylalkyl, said aryloxy, and said phenyl is optionally substituted with 1-3 moieties independently selected from the group consisting of halogen, $C_1$-$C_6$ alkyl, $C_2$-$C_6$ alkenyl, $C_2$-$C_6$ alkynyl, $NR_4R_5$, $N[(CH_2)_2]_2O$, $N[(CH_2)_2]_2NR_4$, $NHSO_2R_4$, $NRC(\!\!=\!\!O)R_5$, $NH_4C(\!\!=\!\!O)OR_4$, $NO_2$, $SO_2NR_4R_5$, $SO_2R_4$; $OR_4$, $C(\!\!=\!\!O)R_4$, $COOR_4$, $CONR_4R_5$, and CN.

16. The compound of claim 15, or a pharmaceutically acceptable salt thereof, wherein $R_1$ is substituted with at least one halogen.

17. The compound of claim 15, or a pharmaceutically acceptable salt thereof, wherein $R_1$ is $C_1$-$C_6$ alkyl or $C_2$-$C_7$ alkenyl, wherein each of said $C_1$-$C_6$ alkyl and said $C_2$-$C_7$ alkenyl is optionally subsiitated.

18. The compound of claim 15, or a pharmaceutically acceptable salt thereof, wherein $R_2$ is $C_1$-$C_6$ alkyl or $C_2$-$C_7$ alkenyl, $R_3$ is H, wherein each of said $C_1$-$C_6$ alkyl and said $C_2$-$C_7$ alkenyl is optionally substituted.

19. The compound of claim 15, or a pharmaceutically acceptable salt thereof, wherein $R_4$, $R_5$, $R_6$, and $R_7$ are each, independently, H, $C_1$-$C_3$ alkyl, $C_2$-$C_4$ alkenyl, halogen, or trifluoromethyl, wherein each of said $C_1$-$C_3$ alkyl and said $C_2$-$C_4$ alkenyl is optionally substituted.

20. A composition, comprising:
a compound of claim 1, or a pharmaceutically acceptable salt thereof; and
a pharmaceutical carrier.

21. A composition, comprising
a compound of claim 15, or a pharmaceutically acceptable salt thereof; and
a pharmaceutical carrier.

22. A method for treating a patient suspected of suffering from a disease associated with excessive estrogen receptor activity, comprising the step of administering to the patient a therapeutically effective amount of a compound of claim 1, or a pharmaceutically acceptable salt thereof.

23. The method of claim 22, wherein the disease is atherosclerosis, myocardial infarction, or congestive heart failure.

24. A method of heating a disorder associated with inflammation in a mammal in need thereof which comprises administering to said mammal an effective amount of a compound of claim 1, or a pharmaceutically acceptable salt thereof, wherein the disorder is ischemia/reperfusion injury or sepsis.

25. The method of claim 22, wherein the disease is inflammatory bowel disease, arthritis, type II diabetes, or rheumatoid arthritis.

* * * * *